United States Patent
Lichty et al.

(10) Patent No.: US 10,925,946 B2
(45) Date of Patent: *Feb. 23, 2021

(54) VACCINATION METHODS

(71) Applicant: Turnstone Limited Partnership, Toronto (CA)

(72) Inventors: Brian Lichty, Brantford (CA); Byram Bridle, Guelph (CA); Yonghong Wan, Hamilton (CA); Jonathan Bramson, Oakville (CA)

(73) Assignee: Turnstone Limited Partnership, Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/630,454

(22) Filed: Jun. 22, 2017

(65) Prior Publication Data
US 2017/0348404 A1 Dec. 7, 2017

Related U.S. Application Data

(63) Continuation of application No. 13/257,115, filed as application No. PCT/CA2010/000379 on Mar. 16, 2010, now Pat. No. 9,707,285.

(60) Provisional application No. 61/160,371, filed on Mar. 16, 2009, provisional application No. 61/160,372, filed on Mar. 16, 2009.

(51) Int. Cl.
A61K 39/00 (2006.01)
C12N 9/02 (2006.01)
A61K 35/13 (2015.01)

(52) U.S. Cl.
CPC .... *A61K 39/0011* (2013.01); *A61K 39/00118* (2018.08); *A61K 39/00119* (2018.08); *A61K 39/001102* (2018.08); *A61K 39/001181* (2018.08); *A61K 39/001182* (2018.08); *A61K 39/001184* (2018.08); *A61K 39/001191* (2018.08); *A61K 39/001192* (2018.08); *C12N 9/0059* (2013.01); *A61K 35/13* (2013.01); *A61K 2039/5256* (2013.01); *C12N 2710/10343* (2013.01); *C12N 2760/20243* (2013.01)

(58) Field of Classification Search
None
See application file for complete search history.

(56) References Cited

U.S. PATENT DOCUMENTS 7,452,723 B2  11/2008  Coffey et al.
2003/0157135 A1  8/2003  Tsuji et al.

FOREIGN PATENT DOCUMENTS

| DE | 60026554 | 9/2006 |
|---|---|---|
| EP | 1716858 | 11/2006 |
| WO | WO002067861 | 9/2002 |
| WO | 2006061643 | 6/2006 |
| WO | 2007025365 | 3/2007 |
| WO | 2008009115 | 1/2008 |
| WO | 2008011726 | 1/2008 |
| WO | 2008094188 | 8/2008 |

OTHER PUBLICATIONS

Hung et al. Therapeutic human papillomavirus vaccines: current clinical trials and future directions. Expert Opin. Biol. Ther. (2008) 8(4):421-439.*
Tanaka et al. Induction of a systemic immune response by a polyvalent melanoma-associated antigen DNA vaccine for prevention and treatment of malignant melanoma. Mol Ther. Mar. 2002; 5(3):291-9.*
Goldberg et al. Comparison of Two Cancer Vaccines Targeting Tyrosinase: Plasmid DNA and Recombinant Alphavirus Replicon Particles. Clin Cancer Res 2005;11(22): 8114-8121.*
Kast, WM (2008). VEEV replicon-based vaccines used in heterologous prime boost strategies induce lifelong protection against cancer and therapy of cervical cancer in mice and robust cell-mediated immunity in rhesus macaques. In: Vaccine Technology II P09, Jun. 1-6, 2008, Algarve, Portugal.*
Suksanpaisan et al. Preclinical Development of Oncolytic Immunovirotherapy for Treatment of HPVPOS Cancers. Molecular Therapy: Oncolytics vol. 10 Sep. 2018, pp. 1-13.*
Diaz, et al., Oncolytic Immunovirotherapy for Melanoma Using Vesicular Stomatitis Virus. Cancer Res 2007; 67(6). Mar. 15, 2007, pp. 2840-2848.
Blechaz, et al., Measles virus as an oncolytic vector platform. Current Gene Therapy, Jun. 2008, vol. 8, No. 3, pp. 162-175.
Phuong, et al., Use of a vaccine strain of measles virus genetically engineered to produce carcinoembryonic antigen as a novel therapeutic agent glioblastoma multiforme. Cancer Res. May 15, 2003; 63(10):2462-2469.
Ritchie, et al., B-Lymphocytes activated by CD40 ligand induce an antigen-specific anti-tumour immune response by direct and indirect activation of CD8(+) T-cells. Scand J Immunol. Dec. 2004;60(6):543-551.
Barber, Vesicular stomatitis virus as an oncolytic vector. Viral Immunol. 2004; 17(4):516-527.
Chuang, et al., Combination of Viral Oncolysis and Tumor-Specific Immunity to Control Established Tumors, Clin Cancer Res 2009; 15(14) Jul. 15, 2009, pp. 4581-4588.

(Continued)

*Primary Examiner* — Nianxiang Zou

(74) *Attorney, Agent, or Firm* — Jones Day

(57) ABSTRACT

In one aspect, a method of treating cancer in a mammal is provided. The method comprises administering to the mammal an oncolytic vector that expresses a tumour antigen to which the mammal has a pre-existing immunity. In another aspect, a method of boosting immune response in a mammal having a pre-existing immunity to an antigen is provided comprising intravenous administration to the mammal of a B-cell infecting vector that expresses the antigen.

23 Claims, 25 Drawing Sheets

(56) References Cited

OTHER PUBLICATIONS

Vigil, et al., Recombinant Newcastle Disease Virus as a Vaccine Vector for Cancer Therapy. The American Society of Gene Therapy, Mol Ther (2008), pp. 1-8.
Kirn, et al., Targeted and armed oncolytic poxviruses: a novel multi-mechanistic therapeutic class for cancer. Nat Rev Cancer. Jan. 2009;9(1):64-71.
Roediger, et al. Heterologous boosting of recombinant adenoviral prime immunization with a novel vesicular stomatitis virus-vectored tuberculosis vaccine. Mol Ther. Jun. 2008;16(6): 1161-9 Epub Mar. 25, 2008.
Bachmann, et al. Immunization with recombinant protein: conditions for cytotoxic T cell and/or antibody induction. Med Microbiol Immunol. Dec. 1994; 183(6):315-24.
Jia, et al. Immunization with single-cycle SIV significantly reduces viral loads after an intravenous challenge with SIV (mac) 239. PLoS Pathog. Jan. 2009;5(1):e1000272, Epub Jan. 23, 2009, pp. 1-19.
Vile, et al., The oncolytic virotherapy treatment platform for cancer. Unique biological and biosafety points to consider. Cancer Gene Therapy 2002, vol. 9, No. 12, pp. 1062-1067.
Ebert et al., Systemic therapy of experimental breast cancer metastases by mutant vesicular stomatitis virs in immune-competent mice. Cancer Gene Therapy (2005) 12, 350-.358.
Majid, et al. Chapter 15, Recombinant Vesicular Stomatitis Virus (VSV) and Other Strategies in HCV Vaccine Designs and Immunotherapy, in Hepatities C Viruses: Genomes and Molecular Biology. Tan SL, editor Norfolk (UK): Horizon Bioscience; 2006.
De Mare et al. Viral vector-based prime-boost immunization regimens: a possible involvement of T-cell competition. Gene Ther. Mar. 2008;15(6):393-403. Epub Nov. 15, 2007.
Van der Burg et al. Pre-clinical safety and efficacy of TA-CIN, a recombinant HPPV16 L2E6E7 fusion protein vaccine, in homologous and heterologous prime-boost regimens. Vaccine. Jun. 14, 2001;19(27):3652-60.
Pol et al.—Maraba Virus as a Potent Oncolytic Vaccine Vector—The American Society of Gene & Cell Therapy, Molecular Therapy vol. 22 No. 2 Feb. 2014.
Liao et al. Single-Dose, Therapeutic Vaccination of Mice with Vesicular Stomatitis Virus Expressing Human Papillomavirus Type 16 E7 Protein. Clinical and Vaccine Immunology, May 2008, p. 817-824 vol. 15, No. 5.
Marshall John L et al: "Phase I study in advanced cancer patients of a diversified prime-and boost vaccination protocol using recombinant vaccinia virus and recombinant nonreplicating avipox virus to elicit anticarcinoembryonic antigen immune response", Journal of Clinical Oncology, American Society of Clinical Oncology, US, vol. 18, No. 23, Dec. 1, 2000 (Dec. 1, 2000), pp. 3964-3973, XP002410670, ISSN: 0732-183X.
Stojdl D F et al: "VSV strains with defects in their ability to shutdown innate immunity are potent systemic anti-cancer agents", Cancer cell, Cell Press, US, vol. 4, No. 4, Oct. 1, 2003 (Oct. 1, 2003), pp. 263-275, XP0022887312, ISSN: 1535-6108, DOI: 10.1 016/S1535-61 08(03)00241-1.
Nina F Rose et al: "Glycoprotein Exchange Vectors Based on Vesicular Stomatitis Virus Allow Effective Boosting and Generation of Neutralizing Antibodies to a Primary Isolate of Human Immunodeficiency Virus Type 1", Journal of Virology, The American Society for Microbioloty, US, vol. 74; No. 23, Dec. 1, 2000 (Dec. 1, 2000), pp. 10903-10910, XP008148240, ISSN:0022-538X, 001:10. 1128/JVI.74.23. 10903-10910 2000.
Riezebos-Brilman A et al. A comparative study on the immunotherapeutic efficacy of recombinant Semliki Forest virus and adenovirus vector systems in a murine model for cervical cancer. Gene Ther. Dec. 2007;14(24):1695-704.
Hung CF et al. Antigen-specific immunotherapy of cervical and ovarian cancer. Immunol Ref. Apr. 2008;222:43-69.
K. Hasegawa: "Dual Therapy of Ovarian Cancer Using Measles Viruses Expressing Carcinoembryonic Antigen and Sodium Iodide Symporter", Clinical Cancer Research, vol. 12, No. 6, Mar. 15, 2006 (Mar. 15, 2006), pp. 1868-1875, XP055047504, ISSN: 1078-0432, DOI: 10.1158/1078-0432.CCR-05-1803.
Vigil Adam et al: "Recombinant Newcastle disease virus as a vaccine vector for cancer therapy", Molecular Therapy: Nov. 2008, vol. 16, No. 11, pp. 1883-1890, XP002689331, ISSN: 1525-0024.
Kaufam Howard et al.: "Phase II randomized study of vaccine treatment of advanced prostrate cancer (E7897): a trial of the Eastern Cooperative Oncology Group", Journal of Clinical Oncology: Official Journal of the American Society of Clinical Oncology Jun. 1, 2004, vol. 22, No. 11, Jun. 1, 2004 (Jun. 1, 2004), pp. 2122-2132, XP002689337, USSB:0732-183X.
Meng Wilson S et al.: alpha-Fetoprotein-specific tumor immunity induced by plasmid prime-adenovirus boost genetic vaccination:, Cancer Research, vol. 61, No. 24, Dec. 15, 2001 (Dec. 15, 2001), pp. 8782-8886, XP002689332, ISSN: 0008-5472.
Pinto A R et al.: "Induction of CD8+ T cells to an HIV-1 antigen through a prime boost regimen with heterologous E1-deleted adenoviral vaccine carriers", The Journal of Immunology, The American Association of Immunologists, US, vol. 171, No. 12, Dec. 15, 2003 (Dec. 15, 2003), pp. 6774-6779, XP002363607, ISSN: 00225-1767.
Vaccari Monica et al.: "Reduced protection from simian immunodeficiency virus SIVmac251 infection afforded by memory CD8+ T cells induced by vaccination during CD+ T-cell deficiency". Journal of Virology Oct. 2008, vol. 82, No. 19, Oct. 2008 (Oct. 2008), pp. 9629-9638, XP002689437, ISSN: 1098-5514.
Boritz Eli et al.: "Replication-competent rhabdoviruses with human immunodeficiency virus type 1 coats and green fluorescent protein: Entry by a pH-independent pathway", Journal of Virology, vol. 73, No. 8, Aug. 1999 (Aug. 1999), pp. 6937-6945, XP002689438, ISSN:0022-538X.
Li Qi-Xiang et al: "Oncolytic virotherapy as a personalized cancer vaccine", International Journal of Cancer, vol. 123, No. 3, Aug. 2008 (Aug. 2008), pp. 493-499, XP002389333, ISSN:0020-7136.
Lichty Brian et al.: "Vesicular stomatitis virus re-inventing the bullet", Trends in Molecular Medicine, vol. 10, No. 5, May 2004 (May 2004), pp. 210-216, XP002689334, ISSN: 1471-4914.
Bridle Bryam W et al.: "Vesicular stomatitis virus as a novel cancer vaccine vector to prime antitumor immunity amenable to rapid boosting with adenovirus", Molecular Therapy: The Journal of the American Society of Gene Therapy Oct. 2009, vol. 17, No. 10, Oct. 2009 (Oct. 2009), pp. 1814-1821, XP002689335, ISSN: 1525-0024.
Bryam W Bridle et al.: "Potentiating Cancer Immunotherapy Using an Oncolytic Virus", Molecular Therapy, vol. 18, No. 8, Aug. 1, 2010 (Aug. 1, 2010), pp. 1430-1439, XP055047841, ISSN: 1525-0016, DOI: 10.1038/mt2010.98.
Chen et al., "Boosting with recombinant vaccinia increases HPV-16 E7-specific T cell precursor frequencies of HPV-16 E7-expressing DNA vaccines," Vaccine (2000) 18:2015-2022.
Fiander et al., "Prime-boost vaccination strategy in women with high-grade, noncervical anogenital intraepithelial neoplasia: clinical results from a multicenter phase II trial," Int J Gynecol Cancer. May-Jun. 2006;16(3):1075-81. (abstract only).
Lin et al., "Boosting with Recombinant Vaccinia Increases HPV-16 E7-Specific T Cell Precursor Frequencies and Antitumor Effects of HPV-16 E7-Expressing Sindbis Virus Replicon Particles," Molecular Therapy (2003) 8(4):559-566.
Mackova et al., "Prime/boost immunotherapy of HPV16-induced tumors with E7 protein delivered by Bordetella adenylate cyclase and modified vaccinia virus Ankara," Cancer Immunol Immunother (2006) 55:39-46.
Rittich et al., "Combined immunization with DNA and transduced tumor cells expressing mouse GM-CSF or IL-2," Oncology Reports (2005) 13: 311-317.
Smyth et al., "Immunological Responses in Women with Human Papillomavirus Type 16 (HPV-16)-Associated Anogenital Intraepithelial Neoplasia Induced by Heterologous Prime-Boost HPV-16 Oncogene Vaccination," Clinical Cancer Research (2004) 10(9): 2954-2961.
Wlazlo et al. "DNA vaccines against the human papillomavirus type 16 E6 or E7 oncoproteins" Cancer Gene Therapy (2004) 11, 457-464.

\* cited by examiner

A

B (a)

(b)

VACCINATION METHODS

CROSS-REFERENCE TO RELATED APPLICATIONS

This application is a continuation of U.S. application Ser. No. 13/257,115, filed Sep. 16, 2011, now U.S. Pat. No. 9,707,285, which is a U.S. national stage of International Patent Application No. PCT/CA2010/000379, filed Mar. 16, 2010, which claims the benefit of U.S. Provisional Application No. 61/160,372, filed Mar. 16, 2009 and U.S. Provisional Application No. 61/160,371, filed Mar. 16, 2009, each of which is incorporated by reference herein in its entirety.

FIELD OF THE INVENTION

The present invention relates generally to methods of vaccinating a mammal, and in particular, to vaccination methods useful to boost immune response as well as methods useful to treat disease.

BACKGROUND OF THE INVENTION

Although many successful vaccination regimens have either eliminated or completely controlled infectious diseases, such as smallpox and polio, it has become apparent that certain pathogens are not readily controlled by current vaccination approaches. For instance, pathogens such as HIV, Mycobacterium tuberculosis and the malaria parasite all resist the humoral immunity that is characteristically generated by traditional vaccines. Significant effort has gone into developing vaccines that can promote potent cellular immunity to these and related pathogens. Similarly, immunization with tumor antigens primarily depends on T cells, especially CD8+ CTL, to recognize and destroy cancer cells because many tumor-associated antigens are intracellular proteins. The induction of cellular immunity, however, is complex and poses substantial problems for vaccinologists. These include difficulties in generating cellular immunity that is of sufficient strength and longevity.

One potential approach to circumvent these problems is through the sequential administration of vaccines using heterologous vectors. Although a typical prime-boost regimen involves DNA- and vaccinia-based vaccines, other combinations using bacteria-virus or two different viruses has also been explored in animal models. The most used poxvirus for vaccination is vaccinia virus, which was used for vaccination against smallpox. Recombinant vaccinia can deliver foreign antigens to the cytoplasm of mammalian cells, thereby allowing them direct access to antigen processing pathways which leads to presentation of antigen-derived peptides in association with MHC Class I and Class II molecules on the cell surface. This property makes vaccinia useful as a recombinant vaccine, particularly for stimulating CD 8+ and CD4+ T cell immune responses. Concern about the capacity of vaccinia virus to replicate in mammalian cells has limited its clinical use and led to the search for safer alternatives.

With respect to the use of viruses to treat disease such as cancer, oncolytic viruses (OV) have been found to cure cancer in animal models if they infect tumors and replicate extensively to mediate complete destruction. However, broad clinical application requires treating immunocompetent hosts bearing malignancies that may have partially intact antiviral mechanisms. An active host immune response against the virus that rapidly eliminates viral replication, leading to incomplete or transient tumor destruction represents an important barrier to success. It has been shown in naive animals that the development of an acquired immune response usually takes less than a week, leaving a small window of opportunity for oncolytic vectors to function. To maximize replication of the administered virus or re-administered virus, a variety of approaches have been tested ranging from outright immunosuppression, to the use of carrier cells (so-called "Trojan horses") and viral cloaking.

Despite the foregoing attempts to address the problems associated with current methods of vaccination, it is desirable to develop more effective methods of generating an immune response in a mammal.

SUMMARY OF THE INVENTION

Novel vaccination methods have now been developed.

Accordingly, in one aspect of the invention, a method of treating cancer in a mammal is provided comprising administering to the mammal an oncolytic vector, wherein the vector expresses a tumour antigen to which the mammal has a pre-existing immunity.

In another aspect, a kit for use in treating cancer is provided comprising a tumour antigen, or a vector expressing a tumour antigen, in an amount suitable to induce an immune response in a mammal, and an oncolytic vector expressing the tumour antigen in an amount suitable to enhance the immune response.

In another aspect of the invention, a method of boosting immune response in a mammal having a pre-existing immunity to an antigen is provided. The method comprises administering to the mammal intravenously a vector expressing the antigen, wherein said vector is capable of infecting B cells.

In a further aspect, a method of boosting immune response in a mammal having a pre-existing immunity to an antigen is provided comprising intravenously administering to the mammal antigen-loaded B-cells.

In yet a further aspect, a kit for use in boosting an immune response in a mammal is provided. The kit comprises an antigen, or a vector expressing the antigen, in a suitable administrable form, and a vector expressing the antigen which is in a form suitable for intravenous administration.

These and other aspects of the invention will become apparent in the detailed description that follows and by reference to the following figures.

DETAILED DESCRIPTION OF THE INVENTION

Figure 1:
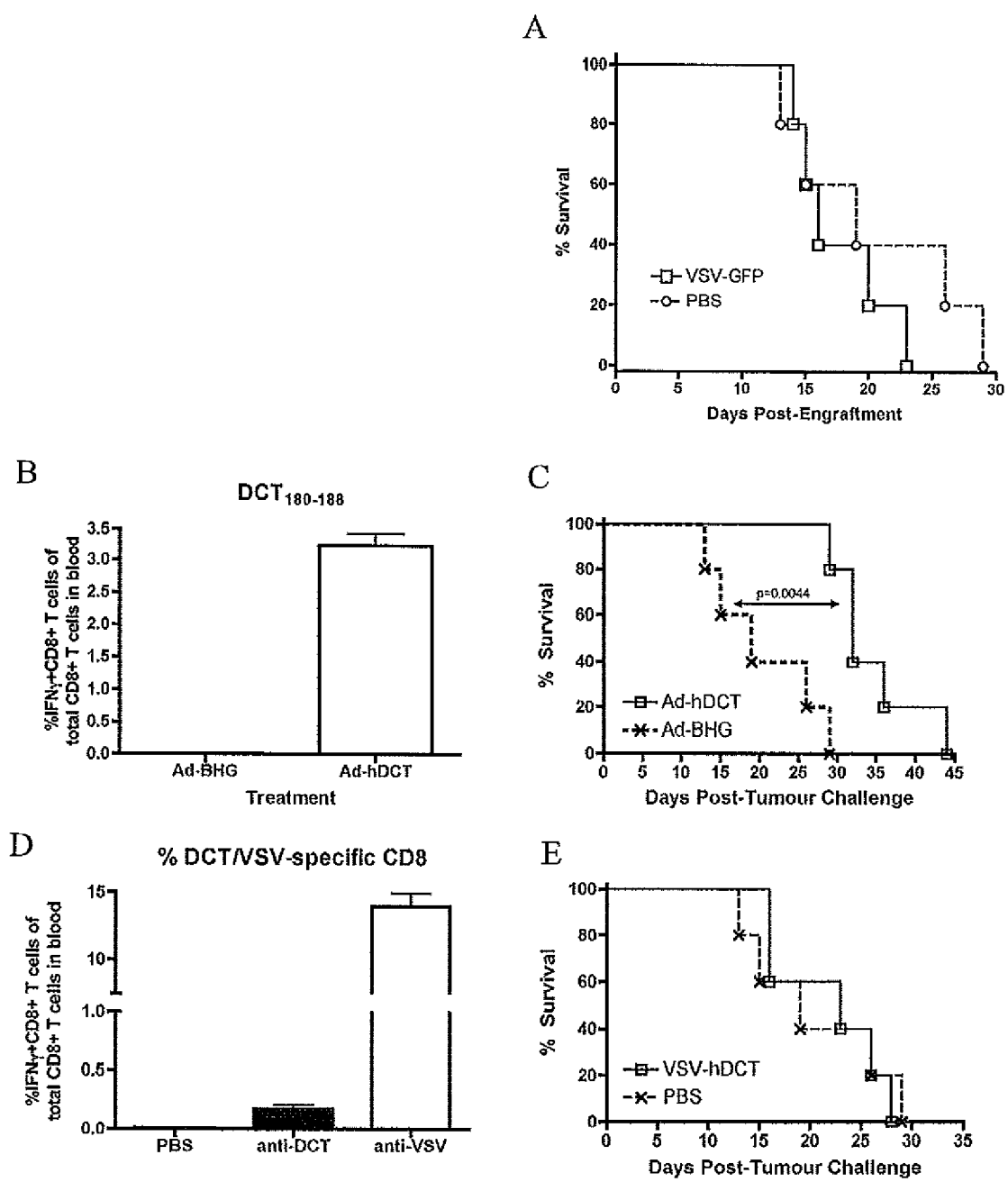
FIG. 1 illustrates the effect of VSV-GFP (A), Ad-hDCT (B and C) and VSV-hDCT (D and E) on tumours in vivo.

A vaccination method useful to treat cancer in a mammal is provided in which an oncolytic vector expressing a tumour antigen, to which the mammal has a pre-existing immunity, is administered to the mammal. The invention provides a method in which the mammal's immune response to the tumour antigen outweighs the mammal's immune response to the oncolytic virus, thereby resulting in effective treatment of cancer.

The present vaccination method is useful to treat cancer in a mammal. The term "cancer" is used herein to encompass any cancer, including but not limited to, melanoma, sarcoma, lymphoma, carcinoma such as brain, breast, liver, stomach and colon cancer, and leukaemia.

The term "mammal" refers to humans as well as non-human mammals.

The method includes administration to the mammal of an oncolytic vector expressing a tumour antigen to which the mammal has a pre-existing immunity. As used herein, the term "pre-existing immunity" is meant to encompass an immunity induced by vaccination with an antigen, as well as a naturally existing immunity within the mammal.

Thus, in one embodiment, to establish a pre-existing immunity, the present method includes a step of vaccinating a mammal with a tumor antigen appropriate to induce an immune reaction against target cancer cells. The tumor antigen may, for example, be a tumor-associated antigen (TAA), e.g. a substance produced in a tumor cell which triggers an immune response in the mammal. Examples of such antigens include oncofetal antigens such as alphafeto-protein (AFP) and carcinoembryonic antigen (CEA), surface glycoproteins such as CA 125, oncogenes such as Her2, melanoma-associated antigens such as dopachrome tautomerase (DCT), GP100 and MART1, cancer-testes antigens such as the MAGE proteins and NY-ESO1, viral oncogenes such as HPV E6 and E7, proteins ectopically expressed in tumours that are usually restricted to embryonic or extra-embryonic tissues such as PLAC1. As one of skill in the art will appreciate, an antigen may be selected based on the type of cancer to be treated using the present method as one or more antigens may be particularly suited for use in the treatment of certain cancers. For example, for the treatment of melanoma, a melanoma-associated antigen such as DCT may be used.

The antigen may be administered per se, or, preferably, administered via a vector, e.g. adenoviral (Ad), poxviral or retroviral vector, a plasmid or loaded antigen-presenting cells such as dendritic cells. Methods of introducing the antigen into the vector are known to those of skill in the art. Generally, the vector will be modified to express the antigen. In this regard, nucleic acid encoding the selected antigen is incorporated into the selected vector using well-established recombinant technology.

The antigen is administered to the mammal in any one of several ways including, but not limited to, intravenously, intramuscularly, or intranasally. As will be appreciated by one of skill in the art, the antigen, or vector incorporating the antigen, will be administered in a suitable carrier, such as saline or other suitable buffer. Following vaccination with a selected tumour antigen, an immune response is generated by the mammal within an immune response interval, e.g. within about 4 days and extending for months, years, or potentially life.

The establish an immune response to the antigen, vaccination using the antigen is conducted using well-established techniques. Accordingly, a selected antigen, or a vector expressing the antigen, may be administered to the mammal, in an amount sufficient to generate an immune response. As one of skill in the art will appreciate, the amount required to generate an immune response will vary with a number of factors, including, for example, the selected antigen, the vector used to deliver the antigen, and the mammal to be treated, e.g. species, age, size, etc. In this regard, for example, intramuscular administration of a minimum of at least about $10^7$ PFU of Adenoviral vector to a mouse is sufficient to generate an immune response. A corresponding amount would be sufficient for administration to a human to generate an immune response.

In another embodiment, the immune response to the antigen may be naturally-occurring within the mammal and a first vaccination step is not necessary to induce the immune response. Naturally-occurring immune response to an antigen may result from any prior exposure to the antigen.

Once an immune response has been generated in the mammal, within a suitable immune response interval, e.g. at least about 24 hours, preferably at least about 2-4 days or longer, e.g. at least about 1 week, an oncolytic virus expressing the tumour antigen is then administered to the mammal in an amount suitable for oncolytic viral therapy, which will vary with the selected oncolytic virus, and the mammal to be treated, as will be appreciated by one of skill in the art. For example, a minimum of $10^8$ PFU of oncolytic VSV administered IV to a mouse is sufficient for oncolytic therapy. A corresponding amount would be sufficient for use in a human.

An oncolytic virus expressing a selected tumour antigen may be prepared by incorporating a transgene encoding the antigen into the virus using standard recombinant technology. For example, the transgene may be incorporated into the genome of the virus, or alternatively, may be incorporated into the virus using a plasmid incorporating the transgene. The present method is not particularly restricted with respect to the oncolytic virus that may be utilized and may include any oncolytic virus capable of destroying tumour, while being appropriate for administration to a mammal. Examples of oncolytic viruses that may be utilized in the present method include rhabdoviruses such as vesiculoviruses, e.g. vesicular stomatitis virus (VSV) and Maraba viruses, Ephemerovirus, Cytorhabdovirus, Nucleorhabdovirus and Lyssavirus viruses, as well as measles, vaccinia, herpes, myxoma, parvoviral, Newcastle disease, adenoviral and semliki forest viruses.

This combination vaccination method provides effective treatment of a cancer in a mammal by administering a target tumour antigen to the mammal thereby stimulating an immune response to the target antigen, followed by enhancement of the immune response by administering to the mammal an oncolytic virus that also expresses the tumour antigen. This method was also found to substantially reduce the mammalian anti-viral response rendering the oncolytic virus a useful contributor with respect to tumour degradation.

A kit is also provided in another aspect of the invention useful in the treatment of cancer. The kit comprises a tumour antigen, or a vector expressing a tumour antigen, in an amount suitable to induce an immune response in a mammal, and an oncolytic vector expressing the tumour antigen in an amount suitable to enhance the immune response. Suitable tumour antigens and oncolytic vectors for inclusion in the kit are described above.

In another aspect of the present invention, a method of boosting an immune response in a mammal having a pre-existing immunity to an antigen is provided. The method comprises intravenous administration to the mammal of the antigen, preferably via a vector that is capable of infecting B-cells. The term "pre-existing immunity" is as defined above and may be achieved as described above.

This method may be utilized to boost immunity with respect to any antigen, including for example, tumour antigens, viral antigens and particularly antigens derived from viral pathogenic organisms such as HIV, HepC, FIV, LCMV, Ebola virus, as well as bacterial pathogens such as mycobacterium tuberculosis. As one of skill in the art will appreciate, the vector may be prepared to express a selected antigen using well-established recombinant technology.

Appropriate vectors for use in delivering an antigen to the mammal are vectors that are capable of infecting B cells, including for example, rhabdoviruses as set out above including vesiculoviruses and Maraba-based viruses. Mutant viral vectors are also appropriate for use in the present method. Mutant attenuated virus, including replication incompetent forms, are particularly advantageous for use in the present method. The antigen may also be administered to the mammal loaded in antigen-presenting cells, such as B cells.

Once the vector is prepared to express the selected antigen, it is administered intravenously to the mammal for optimal immunity boosting. The amount of vector administered will again vary with the selected vector, as well as the mammal. In relation to the pre-existing immunity, the antigen-expressing vector may be administered to the mammal prior to or coinciding with the peak immune response of the pre-existing immunity. The antigen-expressing vector is optimally administered to the mammal to boost the pre-existing immunity following the effector phase of the priming pre-existing immunity.

Such intravenous administration of the antigen-expressing vector, e.g. the boosting vector, results in a significant boost in the immune response to the antigen in comparison to other routes of administration including intramuscular, intraperitoneal, subcutaneous and intranasal. The method provides at least about a 4-fold increase in the immune response as compared with other routes of administration.

A kit for use in boosting an immune response in a mammal is also provided. The kit comprises an antigen, or a vector expressing the antigen, in an amount suitable to induce an immune response to the antigen. The antigen or vector is provided in a suitable administrable form, e.g. in a form suitable for intravenous, intramuscular or intranasal administration. The kit also includes a vector expressing the same antigen which is in a form suitable for intravenous administration, e.g. in a saline or buffered solution. Suitable antigens and vectors for inclusion in the kit are described above.

In a further aspect, a method of boosting immune response in a mammal having a pre-existing immunity to an antigen is provided comprising intravenously administering to the mammal antigen-loaded B-cells. As indicated, intravenous administration of the antigen-loaded B cells results in a significant boost to the pre-existing immune response to the antigen.

Embodiments of the invention are described in the following specific examples which are not to be construed as limiting.

EXAMPLE 1

Materials and Methods

Mice. Female age-matched mice (8-10 weeks old at study initiation), including C57BL/6 (H-2b) and BalB/c (H-2d) mice (Charles River Laboratories, Wilmington, Mass.), were housed in a specific pathogen-free facility. Animal studies complied with Canadian Council on Animal Care guidelines and were approved by McMaster University's Animal Research Ethics Board.

Cells. B16-F10 murine melanoma cells and CT26 colon carcinoma cells were grown in F11-minimum essential medium containing 10% PBS, 2 mM L-glutamine, 1 mM sodium pyruvate, vitamin solution, 0.01 mM non-essential amino acids, 50 μM 2-mercaptoethanol, 100 U/ml penicillin and 100 μg/mL streptomycin (all from Invitrogen, Grand Island, N.Y., USA). HEK293T cells were grown in D-MEM plus 10% FBS while Vero cells were grown in α-MEM plus 10% FBS.

Vectors. Ad-hDCT is an E1/E3-deleted human type 5 Ad that expresses the full-length hDCT gene and AdBHG is an E1/E3-deleted virus that contains no transgene (Lane, C., et al. Cancer Res 64, 1509-1514 (2004); Ng et al. Mol Ther 3, 809-815 (2001)). Recombinant VSV of the Indiana serotype was engineered to express the hDCT by subcloning a hDCT PCR fragment into the XhoI and NheI sites between the G and L genes of the plasmid pVSV-XN (provided by John Rose, Yale University, New Haven, Conn.) as well as a viral genome bearing a ΔM51 mutation in the matrix gene as described in Stojdl, D. F., et al. Cancer Cell 4, 263-275 (2003). Analogous Maraba vectors were constructed using the same strategy. Recombinant genomes were rescued using standard techniques (Lawson et al. Proc Natl Acad Sci USA 1995 Sep. 12;92(19):9009) to generate replication-competent, hDCT-expressing VSV (VSV-hDCT). The parental VSV containing no transgene was rescued as a control virus for some experiments (VSV-MT). A VSV carrying the green fluorescent protein (GFP) was previously described in Stojdl, D. F., et al. Cancer Cell 4, 263-275 (2003) and used to monitor infection in this study (VSV-GFP). Viruses expressing a SIINFEKL-luciferase fusion were used to induce responses versus this ovalbumin-derived epitope as well. Viruses were also constructed expressing LCMV epitopes to vaccinate against this virus. Stocks of VSV were produced from HEK 293T cells and purified by centrifugation on a sucrose gradient. Viral titer was determined by plaque assay on Vero cells.

Peptides. The immunodominant peptide from DCT that binds to H-2Kb (DCT180-188, SVYDFFVWL; shared by human and murine DCT) was synthesized by PepScan Systems (Lelystad, The Netherlands). The H-2Kb-restricted epitope from the N protein of VSV (RGYVYQGL) and a Db-binding murine gp100 peptide (mgp10025-33; EGSRNQDWL) were purchased from Biomer Technologies (Hayward, Calif.).

Stereotactic Surgery. To establish brain tumors, mice received intracranial injections of 1×10³ B16-F10 cells in 2 μl of PBS. Mice were placed in a stereotaxis (Xymotech Biosystems Inc, Quebec, Canada) and an incision made in the scalp to expose the skull under anaesthesia. A needle mounted on a 10 μl Hamilton syringe (Hamilton Company, Reno, Nev.) was positioned over the right hemisphere of the brain, 2.25 mm lateral to Bregma. A small burr hole was drilled through the skull and the bevel of the needle inserted into the brain parenchyma to a depth of 3 mm. Cells were injected over a period of 1 minute. The needle was left in place for 2 minutes prior to withdrawal to minimize reflux along the injection tract. The scalp incision was closed with stainless steel clips that were removed 7-10 days later.

Lung Metastatic Tumours in BalB/c Mice. BalB/c mice were inoculated with 2×10⁵ CT26 cells in 200 μl of PBS via tail vein injection. All untreated mice reached the end point within 24 days.

Vaccination Protocol. Anesthetised mice were immunized by intramuscular (i.m.) injection of 1×10⁸ pfu of Ad vector in 100 μl of PBS (50 μl/hamstring) or injection of 2-10×10⁸ pfu of VSV in 200 μl of PBS into the tail vein (i.v.).

Viral Titering in Tissue Homogenates. To measure intratumoral virus replication, brains or lungs were collected 3 days after i.v. inoculation of VSV vectors, weighed and homogenized prior to titering. Viral titres were quantified by plaque assay on Vero monolayers and are expressed as plaque forming units (PFU) per grain of tissue.

Antibodies. The following monoclonal Abs were used in flow cytometry assays: anti-CD16/CD32 (clone 2.4G2) to block Fc receptors, anti-CD3 (clone 145-2C11), anti-CD8 (clone 53-6.7) for detecting cell surface markers and anti-IFN-γ (clone XMG1.2) for intracellular staining (all reagents from BD Pharmingen, San Diego, Calif., USA).

T cell Preparation and Intracellular Staining. For PBMC (peripheral blood mononuclear cell) collection, blood was collected from the peri-orbital sinus and red blood cells lysed. For TIL (tumour infiltrating lymphocyte) isolation, CNS tumors were dissected from the brains, weighed, minced and subsequently incubated at 37° for 1 h in Hank's buffered saline containing 0.1% collagenase type I (Invitrogen Life Technologies) and DNase (0.1 mg/ml, Sigma-Aldrich, St. Louis, Mo.). Following the digestion, released cells were filtered through a 70-μM strainer and TILs were purified using EasySep CD90-PE system (STEMCELL Technologies, Vancouver, BC). Mononuclear cells from blood and TILs from the brain tumors were stimulated with peptides (1 μg/ml) in the presence of brefeldin A (GolgiPlug, BD Pharmingen, 1 μg/ml added after 1 h of incubation). After 5 h total incubation time, cells were treated with anti-CD16/CD32 and surface markers fluorescently labeled by addition of Abs. Cells were then permeabilized and fixed with Cytofix/Cytoperm (BD Pharmingen) and stained for intracellular cytokines. Data were acquired using a FACSCanto flow cytometer with FACSDiva 5.0.2 software (BD Pharmingen) and analyzed with FlowJo Mac Version 6.3.4 software (Treestar).

Tetramer Staining and BrdU Incorporation Assay. Immunized mice received i.p. injections of 1 mg BrdU 24 h prior to harvest. Lymphocytes from different organs were first stained with APC-conjugated tetramer H-2Kb/SVYDFFVWL and then stained for BrdU using the BrdU staining kit (BD Pharmingen) according to the manufacturer's instructions.

Tissue Staining. For staining of brain paraffin sections, tissue was fixed overnight in 10% formalin, transferred to 70% ethanol, paraffin embedded, and sectioned at a thickness of 5 μm. Sections were stained with hematoxylin and eosin (Sigma).

Statistical Analyses. GraphPad Prism version 4.00 for Windows (GraphPad Software, San Diego, Calif., USA) was used for all graphing and statistical analyses. T cell responses were analyzed by Student's two-tailed t-test or one- or two-way ANOVA. Differences between means were considered significant at p≤0.05. Means plus standard error bars are shown. Survival data were analyzed using the Kaplan-Meier method and the logrank test for trend.

Results

Impact of Oncolysis and Tumor Vaccination in Naïve Hosts

C57BL/6 mice received intracranial injections of 1×10³ B16-F10 cells. One week later mice were treated with intravenous injections of 1×10⁹ pfu of VSV-GFP. Fluorescent microscopy revealed that brains harvested 3 days post-VSV treatment had evidence of intratumoral GFP expression. Macroscopic examination of brains harvested at day 4 post-infection revealed a large reduction in tumor burden in VSV-GFP treated brains. Hematoxylin and eosin stained sections of these brains also indicated this reduction. Survival studies, as shown in FIG. 1A failed to detect prolonged survival following oncolytic VSV-GFP treatment (two groups of five mice treated as above and repeated 3 times with similar results). Alternatively, on day 5 post-engraftment mice were treated with a single intramuscular dose of 1×10⁸ PFU of Ad-hDCT or Ad-BHG. Immunological analysis of peripheral blood was performed on day 14 post-vaccination. The percentage of CD8+ T cells positive for intracellular IFNγ following stimulation with the dominant epitope for DCT are shown in FIG. 1B. Survival data was collected indicating a significant extension of survival in Ad-hDCT vaccinated mice as shown in FIG. 1C. Experiment was repeated 3 times and representative data is shown. In another experiment, on day 5 post-engraftment mice bearing intracranial B16 tumors were treated with a single intravenous dose of 1×10⁹ PFU of VSV-hDCT. Immunological analysis of peripheral blood was performed on day 14 post-VSV administration. The percentage of CD8+ T cells positive for intracellular IFNγ following stimulation with the dominant epitopes for DCT and for the VSV nucleocapsid is shown in FIG. 1D. Survival studies failed to detect prolonged survival following oncolytic VSV-hDCT treatment (two groups of five mice, repeated 3 times with similar results) as shown in FIG. 1E.

Turning the Immune Response Against the Oncolytic Virus (OV) Into a Beneficial One.

Figure 2:
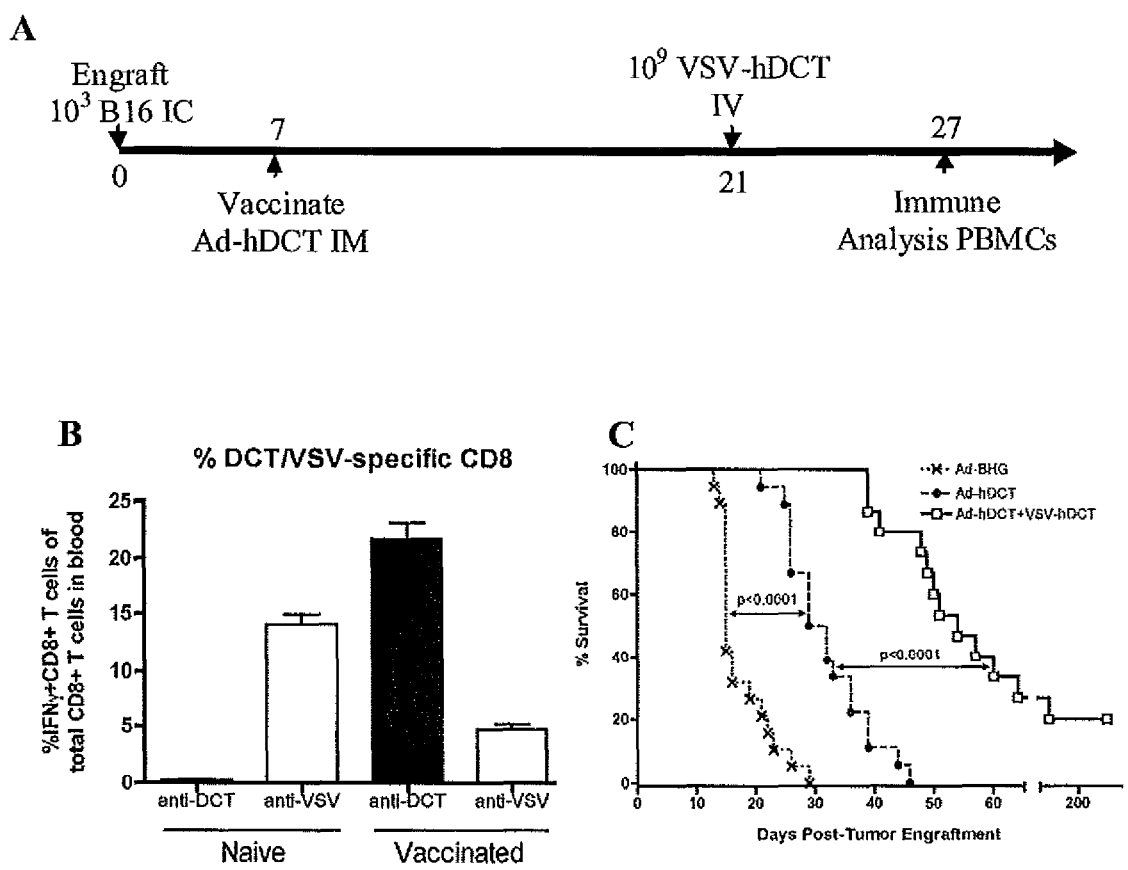
FIG. 2 shows the timeline (A), CD8+ T cell profile (B) and effect on survival (C) for a combination treatment with Ad-hDCT and VSV-hDCT.

The timeline for a combination treatment with Ad-hDCT and VSV-hDCT in which tumour bearing mice are vaccinated on day 5 post-engraftment to generate an anti-DCT response prior to delivery of the oncolytic virus on day 19 is shown in FIG. 2A. Peripheral blood was collected 6 days post-VSV treatment and ICS for IFNγ in response to the dominant epitopes for DCT and for VSV-N was performed. Naive mice displayed a response versus VSV-hDCT that was dominated by the anti-viral response whereas vaccinated mice displayed a response dominated by the anti-DCT response and a reduced anti-VSV response (see FIG. 2B). FIG. 2C shows the pooled survival data for three independent experiments in which mice were treated with empty Ad vector (Ad-BHG), Ad-hDCT alone or Ad-hDCT followed by VSV-hDCT (n=19, n=18 and 5 respectively), and clearly establishes the increased survival with the latter combination.

Immunological Features of Oncolytic Virus Immune Boosting.

Figure 3:
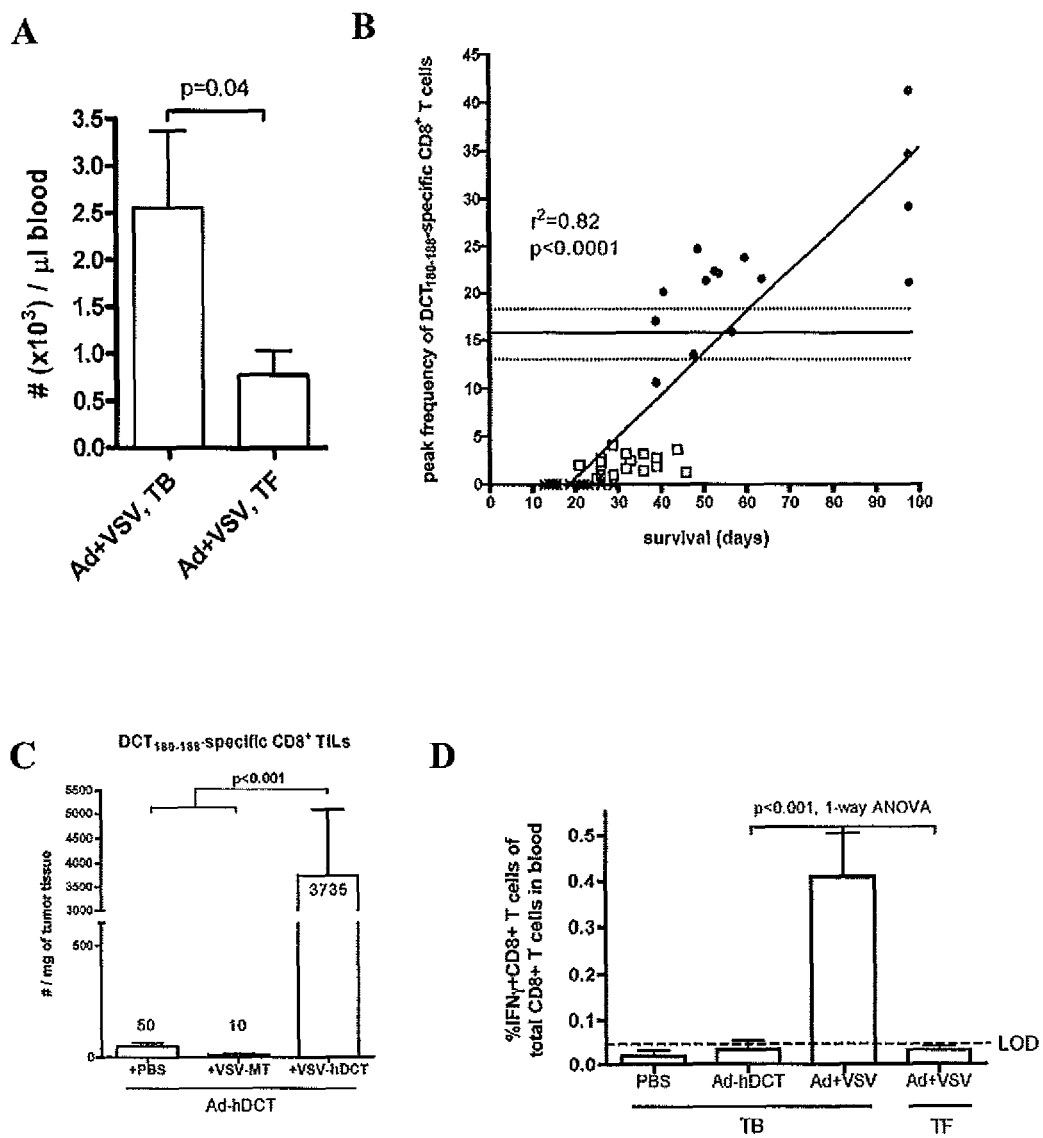
FIG. 3 shows the DCT-specific CD8+ T cell profile (A), correlation of survival to frequency of tumour antigen specific T cells (B), number of DCT T cells (C) and frequency of gp100 T cells (D) following a combination treatment with Ad-hDCT and VSV-hDCT.

Comparison of the numbers of DCT-specific, IFNγ+ CD8+ T cells in the peripheral blood of tumor-bearing (TB) and tumor-free (TF) C57BL/6 mice at the peak of the response post-VSV treatment (TB n=7, TF n=5) is shown in FIG. 3A. Pooled data demonstrating the correlation between the magnitude of the anti-DCT response in the peripheral blood and survival is shown in FIG. 3B. Data includes mice that were mock vaccinated (Ad-BHG, x), Ad-hDCT vaccinated (□) or treated with the Ad-hDCT+VSV-hDCT combination (●). The horizontal lines indicate the mean response achieved in tumor-free mice +/−SEM (dashed lines). The majority of the responses associated with survival >45 days can only be achieved in tumor-bearing animals demonstrating the importance of using an oncolytic virus as the boosting vector. Ad-hDCT vaccinated C57BL/6 mice bearing intracranial B16-F10 tumors were subsequently treated with PBS, VSV-MT (no transgene) or VSV-hDCT. Seven days later tumours were collected and IFNγ+ tumor-infiltrating lymphocytes (TILs) responsive to DCT180-188 peptide were enumerated as shown in FIG. 3C. Gp100-responsive CD8+ T cells were enumerated by ICS for IFNγ demonstrating that combination therapy of tumor-bearing (TB) animals induces epitope spreading (FIG. 3D).

Impact of Vaccination on OV Replication.

Figure 4:
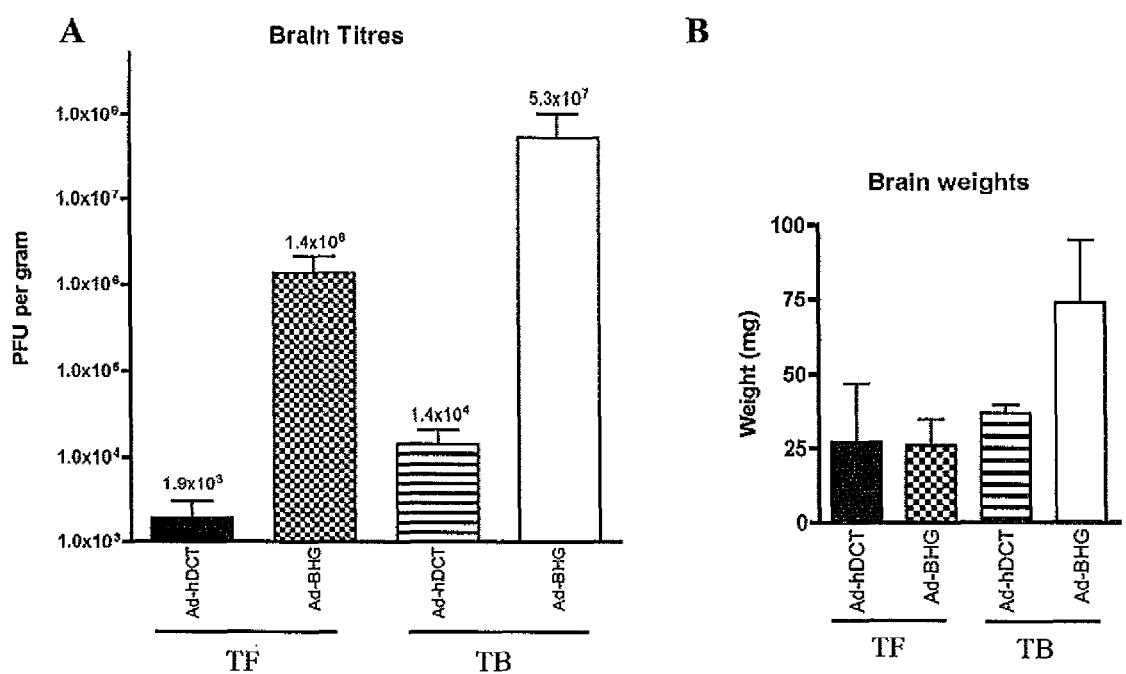
FIG. 4 demonstrates viral titres (A) and brain weights (B) in tumour-bearing mice following Ad-hDCT vaccination and subsequent treatment with VSV-hDCT.

Tumor-free (TF) or B16-F10 tumor-bearing (TB) C57BL/6 mice were immunized i.m. with Ad vectors. Fourteen days after Ad treatment, mice were given VSV-hDCT via i.v. injection and the brains were weighed and homogenized 3 days after VSV inoculation. Viral titres were quantified by plaque assay on Vero monolayers and are expressed as PFU per gram of brain tissue (FIG. 4A). Brain weights are summarized in FIG. 4B. Data were pooled froth two experiments with 5 mice per group.

Kinetics of T Cell Replication Following VSV-hDCT Treatment.

Figure 5:
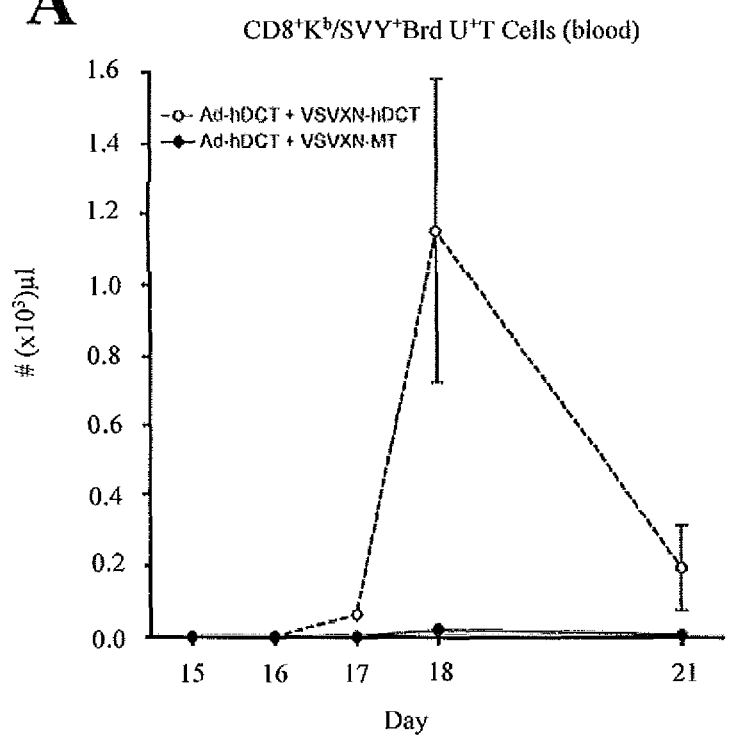
FIG. 5 shows the time course for expansion of DCT specific CD8+ T cells in blood (A), spleen (B) and cervical lymph nodes (C) following VSV-hDCT treatment of Ad-hDCT primed hosts.
Figure 5:
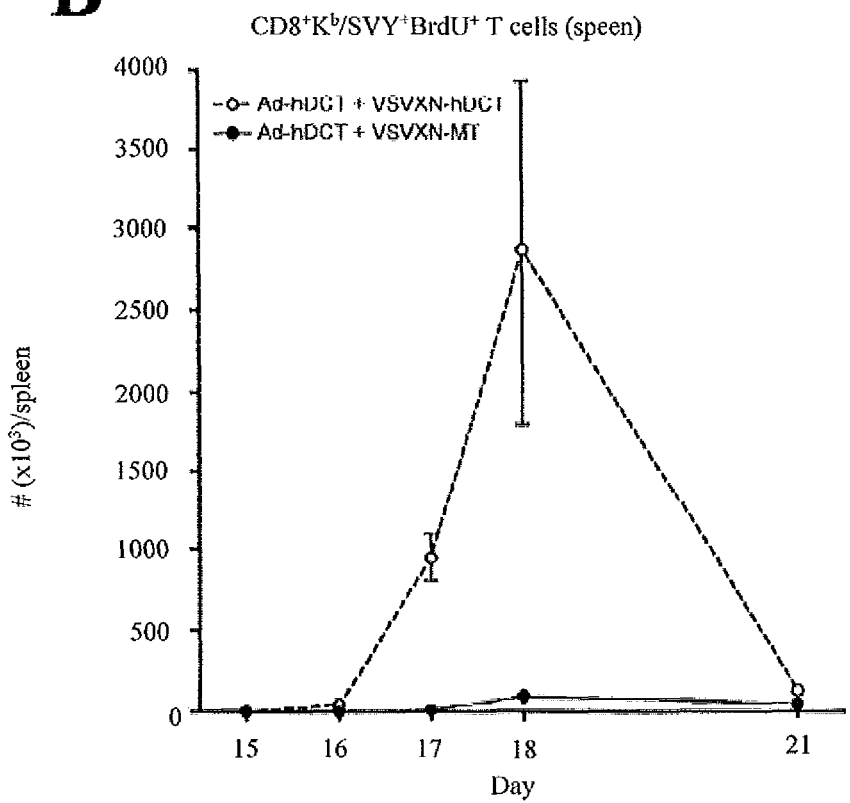
Figure 5:
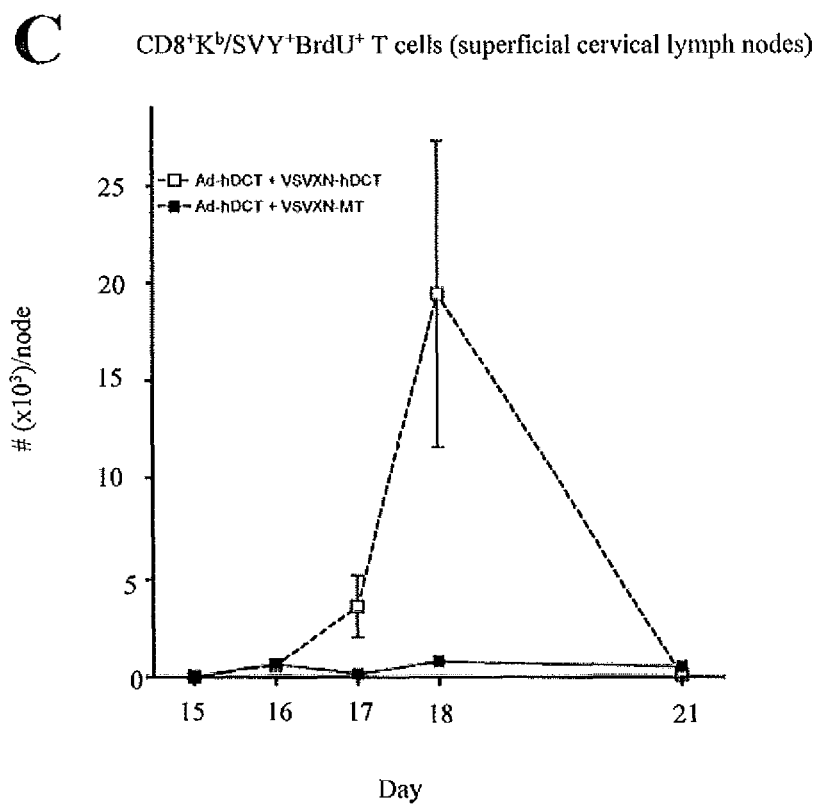

Tumor-free C57BL/6 mice were immunized with Ad-hDCT for 14 days prior to VSV-hDCT inoculation. Immunized mice received i.p. injections of ling BrdU 24 h prior to harvest. Tissues were harvested every 24 hr to monitor T cell proliferation over 7 days. The proliferation of antigen-specific CD8+ T cells in the blood (FIG. 5A), spleen (FIG. 5B) and cervical lymph nodes (FIG. 5C) was determined by co-staining with an antibody for BrdU and tetramer H-2Kb/SVYDFFVWL. Each symbol represents 5 mice and the experiment was repeated twice with similar results.

Impact of Vaccination on Oncolysis in a Lung Metastatic Model.

Figure 6:
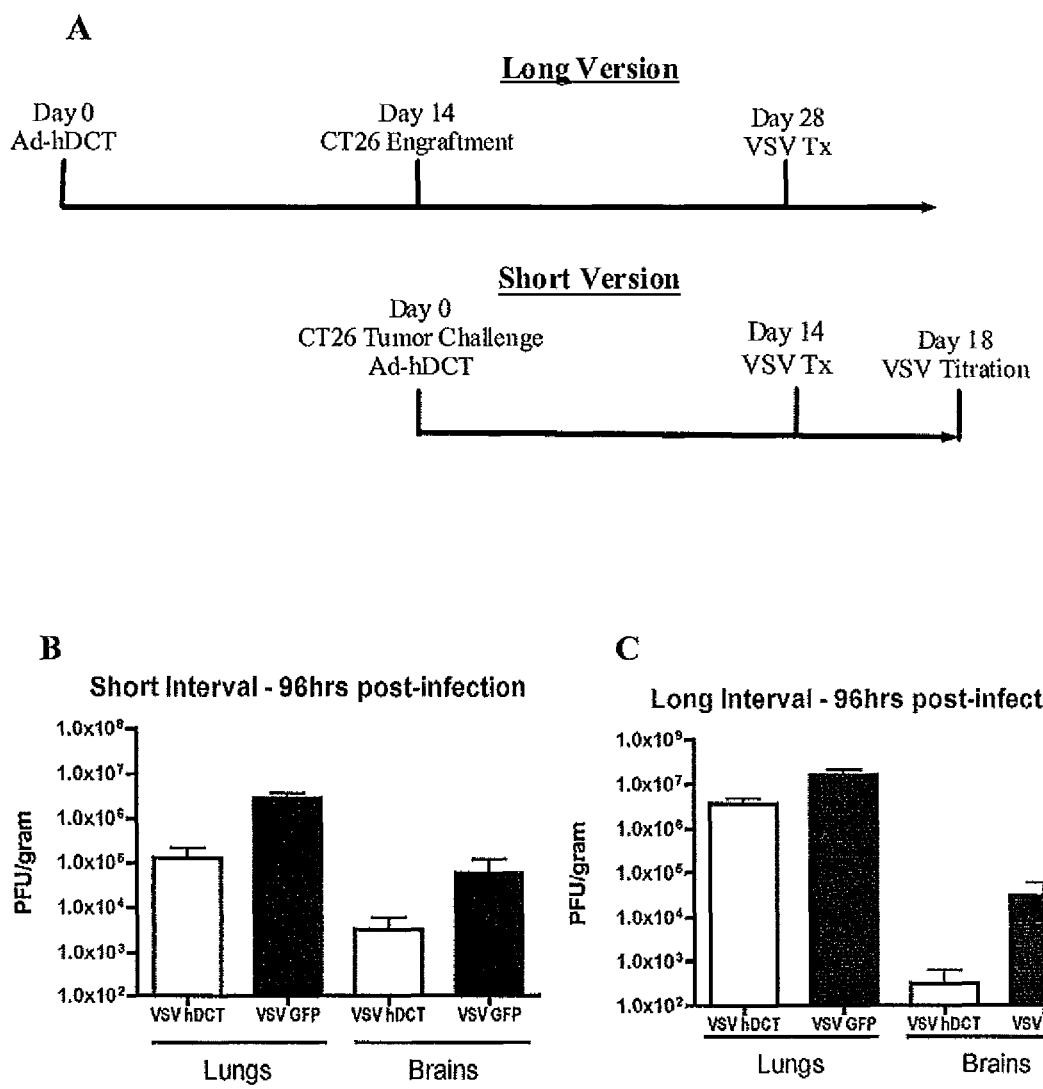
FIG. 6 summarizes the time course for short and long interval treatment regimens (A), and VSV titres in the lungs and brains of mice following the short interval (B) and long interval (C) time course immunization and treatment protocols.

BalB/c mice were immunized i.m. with 10⁸ PFU of Ad-hDCT 14 days before (long interval) or on the same day (short interval) of CT26 tumor engraftment (2×10⁵ cells, i.v. injection) as shown in the time-line (FIG. 6A). Fourteen days after tumor inoculation, mice were treated with 2×10⁸ PFU of VSV-hDCT or VSV-GFP via tail vein injection. Whole lungs were harvested and homogenized 4 days after VSV treatment. Viral titres were quantified by plaque assay on Vero monolayers and are expressed as PFU per gram of tissue (see FIGS. 6B and 6C, respectively). Data were pooled from two experiments with 5 mice per group.

Increased Interval Between Prime and Boost Enhances Magnitude of Response.

C57BL/6 mice were initially immunized with an i.m. dose of 10⁸ PFU of Ad-hDCT. Fourteen or 100 days later, mice were given 10⁹ PFU of VSV-hDCT via tail vein injection. The percentage (FIG. 7A) or number (FIG. 7B) of DCT-specific, IFNγ-secreting CD8+ T cells in the blood was quantified by FACS analysis 7 days post VSV treatment. Each bar represents 5 mice.

Maraba-Based Oncolytic Vaccine Vectors

Figure 8:
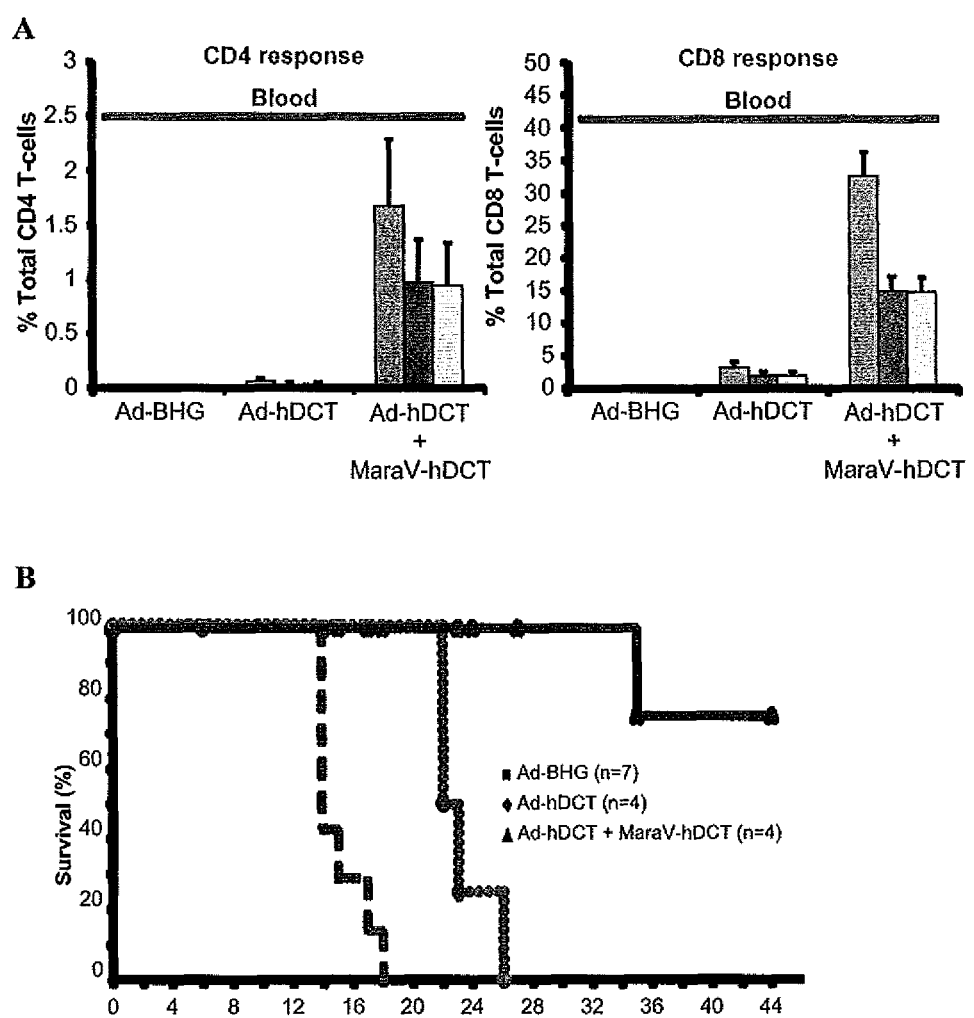
FIG. 8 illustrates the immune analysis (A) and survival data (B) following treatment of tumours with a combination treatment of Ad-hDCT vaccination and oncolytic Maraba-hDCT.

C57/B6 mice bearing intracranial B16F10 tumours were vaccinated with Ad-BHG (empty vector, negative control) or Ad-hDCT (1×10⁸ PFU IM). One group subsequently received a single intravenous dose of Maraba-hDCT (2×10⁹ PFU). Immune analysis was performed on peripheral blood T cells 5 days later (three bars per treatment, left bar is IFNγ+, middle is TNFα+ and right bar is double positive in each case) (FIG. 8A) and survival data was recorded (FIG. 8B).

Vaccination With Antigen-Loaded Dendritic Cells

Figure 9:
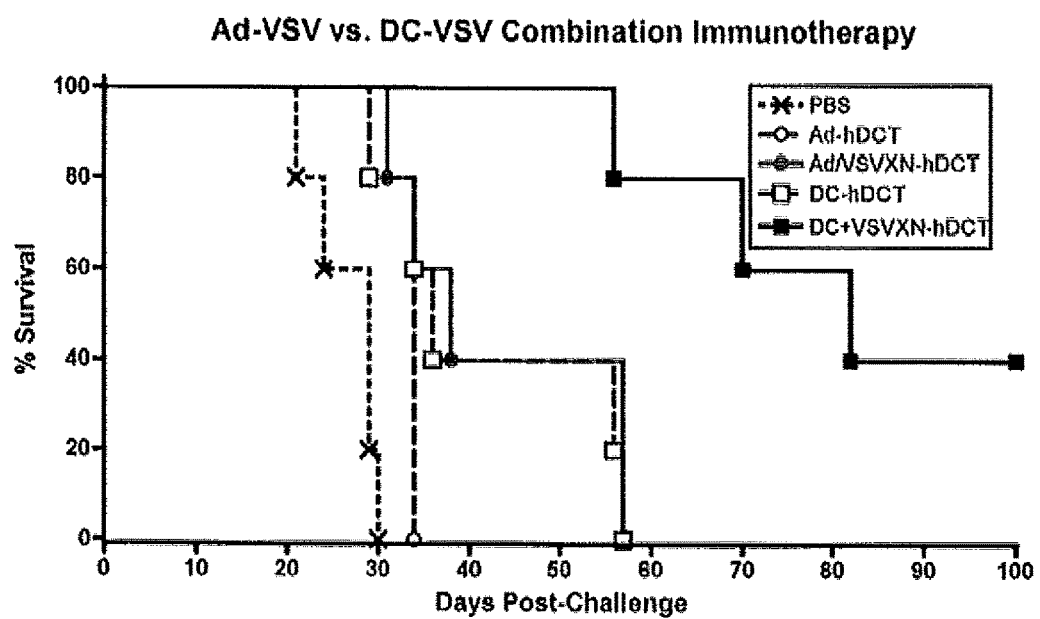
FIG. 9 illustrates survival data (A) and median survival (B) of a combination treatment using dendritic cell vectors to deliver the DCT antigen (DChDCT)
Figure 9:
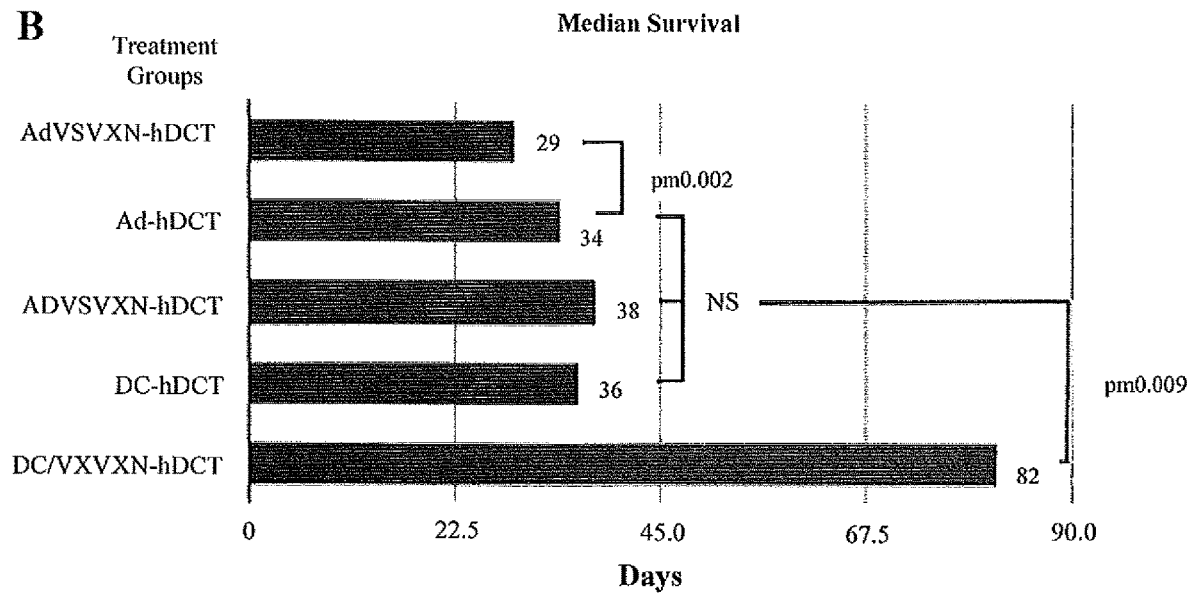

C57/B6 mice were engrafted intravenously with B16F10 cells. Mice were vaccinated with Ad-hDCT or hDCT-loaded dendritie cells (DCs) alone or in combination with subsequent IV delivered VSV-hDCT. Survival data was collected, as shown FIG. 9A. Two mice treated with the combination of DChDCT+VSVhDCT were long-term survivors (sacrificed at 100 days post-engraftment, lungs were clear). Ad-vaccinated groups and the DC-vaccinated group all displayed significantly greater median survival versus PBS treated group while the combination DC-hDCT+VSV-hDCT treated group displayed the greatest median survival. (FIG. 9B).

Vaccination With Antigen-Loaded Vaccinia Viral Vector

Figure 10:
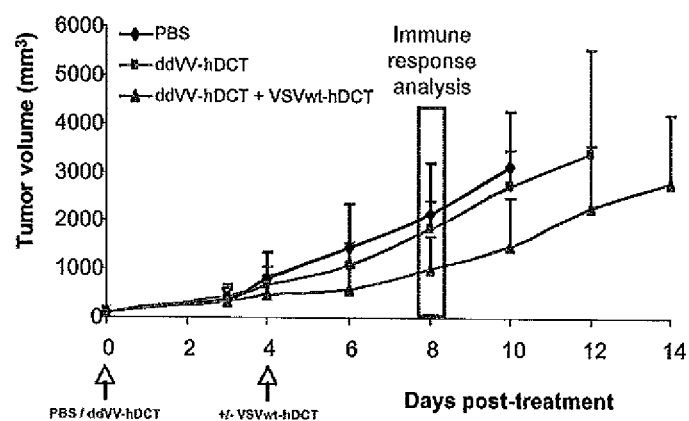
FIG. 10 illustrates the effect on tumour volume (A) and survival (B) with the use of double-deleted vaccinia vector to deliver DCT antigen (ddVV-hDCT) in a combination treatment.
Figure 10:
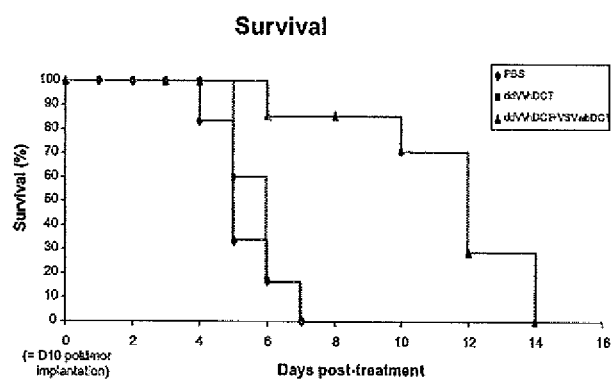

Day 10 subcutaneous B16F10 melanoma tumours were treated with PBS, double-deleted vaccinia-hDCT (ddVV-hDCT, $1\times10^8$ PFU IT) alone or ddVV-hDCT followed four days later by VSV-hDCT ($2\times10^9$ PFU IV). Tumour volumes (FIG. 10A) and survival data (FIG. 10B) are provided and illustrate the increased response for the combination therapy.

Discussion

An aggressive intracranial (i.c.) B16 melanoma model was utilized in an immunocompetent host using melanoma-associated antigens. In this model, C57BL/6 mice were engrafted with $1\times10^3$ B16-F10 cells through i.e. injection and the median survival time following tumor delivery was 15 days (cumulative data for untreated controls, n=41). To evaluate the efficacy of VSV treatment, mice carrying 5-day-old B16 tumors were treated with a single intravenous (i.v.) dose of $1\times10^9$ VSV-GFP. The tumor was infected with VSV resulting in a clear reduction in tumor volumes as expected. However, this effect was transient and failed to translate into a survival benefit (FIG. 1a).

In another approach, the treatment of i.e. B16 melanoma via tumor vaccination was tested. C57BL/6 mice were engrafted with an i.e. dose of $1\times10^3$B16 cells and these were treated intramuscularly (i.m.) with $1\times10^8$ PFU of Ad-hDCT 5 days post-engraftment. CD8+ T cell response against an immunodominant epitope DCT180-188 (identical between human and mouse) was evident in peripheral blood one-week post-vaccination and peaked at day 12-14 (~3.5% IFN-γ+ CD8+ T cells, FIG. 1b). Compared to VSV treatment, Ad-hDCT vaccination significantly extended survival (median time to death 32 days vs. 19 days, P=0.0044) (FIG. 1c) but was unable to cure any of the mice. No DCT-specific T cells or protection was measured in mice immunized with a control vector Ad-BHG or PBS.

In a further approach, VSV was engineered to express hDCT (VSV-hDCT) and treated mice having i.e. B16-F10 tumors with the VSV-hDCT vector. This vector induced a small anti-DCT CD8+ T cell response (0.26%, FIG. 1d) which was 12-times smaller than that elicited by Ad-hDCT (3.2%, FIG. 1b). However, a high level of CD8+ T cells against an epitope from the VSV nucleoprotein was detected following VSV-hDCT treatment (14.0%, FIG. 1d) suggesting that the antiviral response dominated the immunological outcome. Similar to the observation with VSV-GFP (FIG. 1a), treatment with VSV-hDCT did not provide any survival benefit (FIG. 1e). Thus the potent antiviral immune response elicited by the oncolytic virus not only causes the oncolytic impact of the vector to be transient, but also dominates attempts to directly induce immune responses against the tumor-associated antigen (TAA) transgene.

In a further approach, an immune response against a defined tumor antigen was induced followed by treatment with an oncolytic virus expressing that same antigen. C57BL/6 mice bearing 7-day-old i.e. B16 tumors were treated by i.m. injection of $1\times10^8$ PFU of either Ad-BHG or Ad-hDCT. Fourteen days later, mice were given a single i.v. dose of VSV-GFP or $1\times10^9$ PFU of VSV-hDCT (FIG. 2a). As summarized in FIG. 2b, Ad-hDCT immunization followed by VSV-hDCT in tumor-bearing mice resulted in 22% of blood-derived CD8+ T cells being DCT-specific; 7-fold (compared to FIG. 1b) or 85-fold (compared to FIG. 1d) higher than either vector treatment alone. Furthermore, not only did this combination significantly enhance the immune response to the TAA, it actually reduced the magnitude of the anti-VSV CD8+ T cell response as compared to that observed following exposure of a nave mouse to this OV (from 14% to 4.7% of blood-derived CD8+ T cells; FIG. 2b), demonstrating an inversion of the immune response against the oncolytic vaccine virus where the anti-tumoral response now dominated over anti-viral immunity. Most importantly, the combination therapy led to a further extension in median survival, i.e. a synergistic effect (15 days median survival with Ad-BHG alone, 30.5 days median survival with Ad-hDCT alone, 54 days median survival with combination treatment) and 20% of mice treated in this fashion displayed a long-term, durable cure (FIG. 2c) following just one dose of each vector.

The magnitude of the anti-DCT T cell response was greater in tumor-bearing animals than in tumor-free animals demonstrating the advantage of using a replicating OV to deliver the transgene in the presence of a tumor (FIG. 3a). Furthermore, survival was directly correlated with the level of DCT-specific CD8+ T cells where the greatest extension to survival was only achieved when the magnitude of this immune response exceeded what could be generated in tumor-free hosts (FIG. 3b). Thus maximal therapeutic effect was mediated through replication of the boosting oncolytic vector within the tumor. As well, the frequency of tumor-infiltrating CD8+ T cells specific for DCT was significantly higher in VSV-hDCT treated animals as compared to those treated with the VSV-MT control virus, indicating that treatment with VSV-hDCT not only resulted in an overall increase in the number of antigen-specific CD8+ T cells in the periphery but also enhanced their recruitment into the tumor (FIG. 3c). Interestingly, a CD8+ T cell response against GP100, another TAA with which the mice were not vaccinated, was detected providing evidence of epitope spreading likely resulting from enhanced tumor destruction by both anti-DCT CTL and viral oncolysis because an anti-GP100 response was not measured with either treatment alone (FIG. 3d).

Although the observations described above suggest that VSV-hDCT remains oncolytic in the presence of immune response against the vector transgene, the impact of such pre-existing immunity on VSV replication was evaluated. Tumor-free mice and mice bearing intracranial B16-F10 tumors were treated with Ad-hDCT or Ad-BHG. Fourteen days later, mice were given an i.v. dose of $1\times10^9$ PFU VSV-hDCT. Brains were harvested 42 hrs post-VSV delivery and viral titres were determined. In mock-vaccinated mice both tumor-free and tumor-bearing brains displayed abundant VSV-hDCT replication, with tumor-bearing brains displaying a viral titre 50 times higher (FIG. 4a). As mock vaccination did not impede tumor growth these mice had a significant tumor burden (FIG. 4b) and were very near endpoint at the time of euthanasia. In the Ad-hDCT vaccinated mice the VSV titres were much lower, however the tumor-bearing brains still exhibited a higher VSV-hDCT titre (FIG. 4a) even though these brains had minimal tumor burden at this time-point (FIG. 4b). Thus, VSV was still able to infect and replicate in this residual tumor despite pre-existing immunity to the vector transgene. To determine the time lag for expansion of DCT-specific CD8+ T cells by VSV-hDCT, mice were boosted with VSV-hDCT and received BrdU 24 hrs prior to tissue harvests that included spleens and lymph nodes. Data summarized in FIG. 5 indicate that expansion of CD8+ T cells was not detected until day 3 post-VSV-hDCT treatment. These data suggest that the oncolytic vaccine vector had at least 3 days to replicate in the presence of the primary immune response against the TAA transgene prior to the large expansion in TAA-specific T cells observed post-treatment.

As Ad-hDCT had a large impact on tumor burden, it was difficult to quantitatively analyze the impact of a pre-existing immune response against a transgene on viral replication in the B16 model. Therefore, this effect was measured in a different tumor model where DCT was not a tumor antigen. This allowed a comparison where mice had similar tumor burdens regardless of vaccination and also allowed for flexibility with regards to the interval between vaccination and viral oncolysis. To this end, a CT26 colon carcinoma lung metastatic model was selected where DCT was irrelevant. Mice were inoculated i.v. with CT26 cells and vaccinated i.m. with Ad-hDCT on the same day. Fourteen days later, mice received $2 \times 10^8$ PFU of either VSV-hDCT or VSV-GFP via i.v. injection. To measure viral replication, mice were euthanized 96 hrs post-VSV administration and lungs and brains were collected for determination of VSV titres by plaque assay (FIG. 6a). An approximately 1.5 log reduction of viral titres was observed in both the lungs and brains of VSV-hDCT treated animals, as compared to VSV-GFP controls (FIG. 6b). Interestingly, however, there was a smaller reduction in VSV-hDCT lung titres if mice were immunized 14 days prior to CT26 engraftment (27 days before VSV-hDCT treatment) (FIG. 6c), suggesting an increased interval between these two treatments can potentially minimize the trade-off in oncolysis. A significant reduction in VSV-DCT brain titres (FIG. 6c) was also observed demonstrating that prior vaccination against a non-structural transgene encoded by an oncolytic virus (OV) reduces OV replication in normal tissues and thus enhances the safety profile of the OV.

Figure 7:
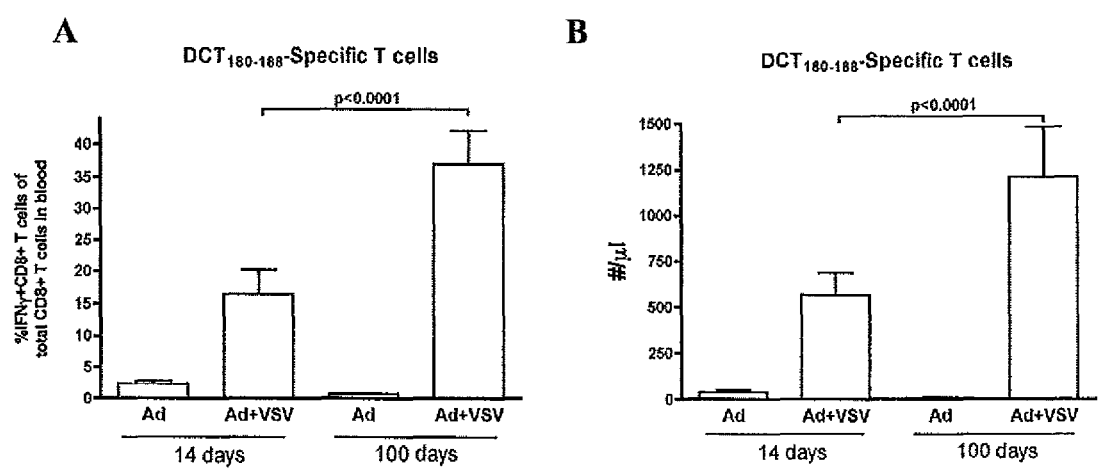
FIG. 7 shows the percentage (A) and number (B) of DCT specific CD8+ T cells in blood when treated with VSV-hDCT either 14 or 100 days following Ad-hDCT immunization.

The reduction in oncolysis can be further minimized by increasing the interval between vaccination and OV administration, as the frequency of antigen-specific effectors subsides over time. A further benefit of extending the interval between vaccination and viral oncolysis can be demonstrated in tumor-free animals where the mean frequency of CD8+ T cells specific for the immunodominant epitope of DCT reached 37% (double the level seen when done at 14 day timepoint) if VSV-hDCT was administered 100 days after Ad-hDCT (FIG. 7).

In view of the foregoing, a treatment strategy that effectively uses tumor vaccination to modify the immune response against an engineered oncolytic viral vector in such a manner so as to allow for a transient viral oncolysis that leads directly to a massive anti-tumoral immune response is demonstrated. By rigging the system such that the dominant immune response versus the oncolytic virus also happens to be an anti-tumoral immune response functions to extend the impact of the viral vector through this immune reaction. Thus, engineering oncolytic viruses to express natural tumor antigens may induce a weak T cell response against the tumor antigen but this response is entirely overshadowed by the immune response against viral antigens. Although prior immunization against an oncolytic vector transgene may appear to be counter-intuitive as it may impair viral delivery or replication, the present results demonstrated that the oncolytic vaccine became more potent under these circumstances since it dramatically amplified the pre-existing anti-tumoral immunity while retaining oncolytic activity, leading to significantly improved clinical outcomes. Surprisingly, pre-existing immunity did not prevent intratumoral viral replication and large immunological benefit of this approach makes this a reasonable trade-off. While this enhanced antigen-specific response may further reduce replication of the OV, the data from BrdU-labelled mice indicated there is at least a 3-day window of opportunity for viral oncolysis. In fact, recruitment of CTL into the tumor at that point is desirable and enhances clearance of both the virus and the tumor.

An additional benefit of this approach is the enhanced safety profile exhibited by the oncolytic vaccine vector. The data demonstrates intracranial infection by VSV following intravenous delivery, however, viral titers were lower in the brains of immunized animals and most strikingly, there was no hind-limb paralysis in any of the mice that had been vaccinated against the viral transgene even though wild-type VSV was used. This combination therapy was also tested with an interferon-inducing mutant of VSV expressing hDCT and resulted in comparable survival in the intracranial B16 model (not shown) indicating that this approach can be successfully combined with other means of viral targeting and attenuation.

The present combination therapy method can utilize various methods of generating a pre-existing antigen immune response (viral, plasmid and cellular), and can also utilize various oncolytic vaccine vectors including VSV and Maraba.

EXAMPLE 2

Materials and Methods

Viruses—VSV vectors used were constructed using a plasmid genome bearing a wildtype M gene (pVSV-XN) or an M protein mutant of the Indiana serotype (($\times$)M51-VSV) and were created by subcloning PCR fragments between the XhoI and NheI sites of the plasmids pVSV-XN or p$\Delta$M5. VSV/SIINFEKL-Luc (VSV/SIIN) contains a modified version of luciferase bearing the immunodominant class-I epitope from OVA (SIINFEKL) tagged to the N-terminus. VSV/hDCT carries a human melanoma-associated antigen, dopachrome tautomerase (DCT). VSV/GFP harbors the green fluorescent protein and the control virus, VSV/MT, contains no transgene. VSV vectors were propagated in 293T cell cultures and purified by centrifugation on a sucrose gradient. Double-deleted vaccinia virus-hDCT (ddVV-hDCT) is a recombinant, thymidine kinase and vaccinia growth factor double-deleted vaccinia virus engineered to express hDCT. Vaccinia was grown on CV1 cells.

Peptides—The immunodominant peptide from DCT that binds to H-2K$^b$ (DCT$_{180-188}$, SVYDFFVWL; shared by human and murine DCT) (Parkhurst et al, 1998) and a K$^b$-binding peptide from OVA (SIINFEKL) were synthesized by PepScan Systems (Lelystad, The Netherlands).

Vaccination Protocol—Anesthetised mice were immunized by i.m. injection of $1 \times 10^8$ pfu of Ad vector in 100 µl of PBS (50 µl/hamstring) and followed by i.v. injection with $1-2 \times 10^9$ pfu of VSV in 200 µl of PBS into the tail vein. The interval ranges from 8 to 233 days.

Antibodies—The following monoclonal Abs were used in flow cytometry assays: anti-CD16/CD32 (clone 2.4G2) to block Fc receptors, anti-CD3 (clone 145-2C11), anti-CD4 (clone RM4-5), anti-CD8 (clone 53-6.7) for detecting cell surface markers and anti-IFN-$\gamma$ (clone XMG1.2) and anti-TNF-$\alpha$ (clone MP6-XT22) for intracellular staining (all reagents from BD Biosciences, San Diego, Calif., USA). Immunodepletion studies were conducted with the mAbs GK1.5 (anti-CD4) and/or 2.43 (anti-CD8) from ATCC. Purified mAbs (250 µg in 500 µl saline) were injected i.p. two days apart and then twice a week thereafter at a maintenance dose of 200 µg per treatment. The efficiency of specific depletion of lymphocyte subsets was >98% as measured by flow cytometry.

T cell Preparation and Intracellular Staining—Blood was collected from the peri-orbital sinus and red blood cells lysed. Spleens and lymph nodes were incubated in Hank's buffered salt solution (HBSS) with 0.05 mg/ml of collagenase type I (Invitrogen Life Technologies) at 37° for 30 min. and then pressed between microscope slides to generate single-cell suspensions. For TIL isolation, CNS tumors were dissected from the brains of PBS-perfused mice, then weighed, minced and subsequently incubated at 37° for 45 min. in HBSS containing 0.5 mg/ml collagenase type I, 0.2 mg/ml DNAse and 0.02 mg/ml hyaluronidase (Sigma-Aldrich, St. Louis, Mo.). Following digestion, released cells were filtered through a 70-µM strainer and TILs were purified using the EasySep CD90.2-PE system (STEMCELL Technologies, Vancouver, BC). Prepared mononuclear cells were stimulated with peptides (1 µg/ml) in the presence of brefeldin A (GolgiPlug, BD Pharmingen, 1 µg/ml added after 1 h of incubation). After 5 h total incubation time cells were treated with anti-CD16/CD32 and surface markers fluorescently labeled by the addition of Abs. Cells were then permeabilized and fixed with Cytofix/Cytoperm (BD Pharmingen) and stained for intracellular cytokines. Data were acquired using a FACSCanto flow cytometer with FACSDiva 5.0.2 software (BD Pharmingen) and analyzed with FlowJo Mac Version 6.3.4 software (Treestar).

B Cell Isolation and culture—Splenic B cells were isolated by negative selection using a MACS kit (Miltenyi) to remove no0-B cells. B cells were cultured in IMDM plus FCS and muIL2 for 4 days prior to infection with Ad or VSV vectors at an MOI of 25 for 2 hours prior to washing and administration via the tail vein into recipient mice.

Results

Figure 11:
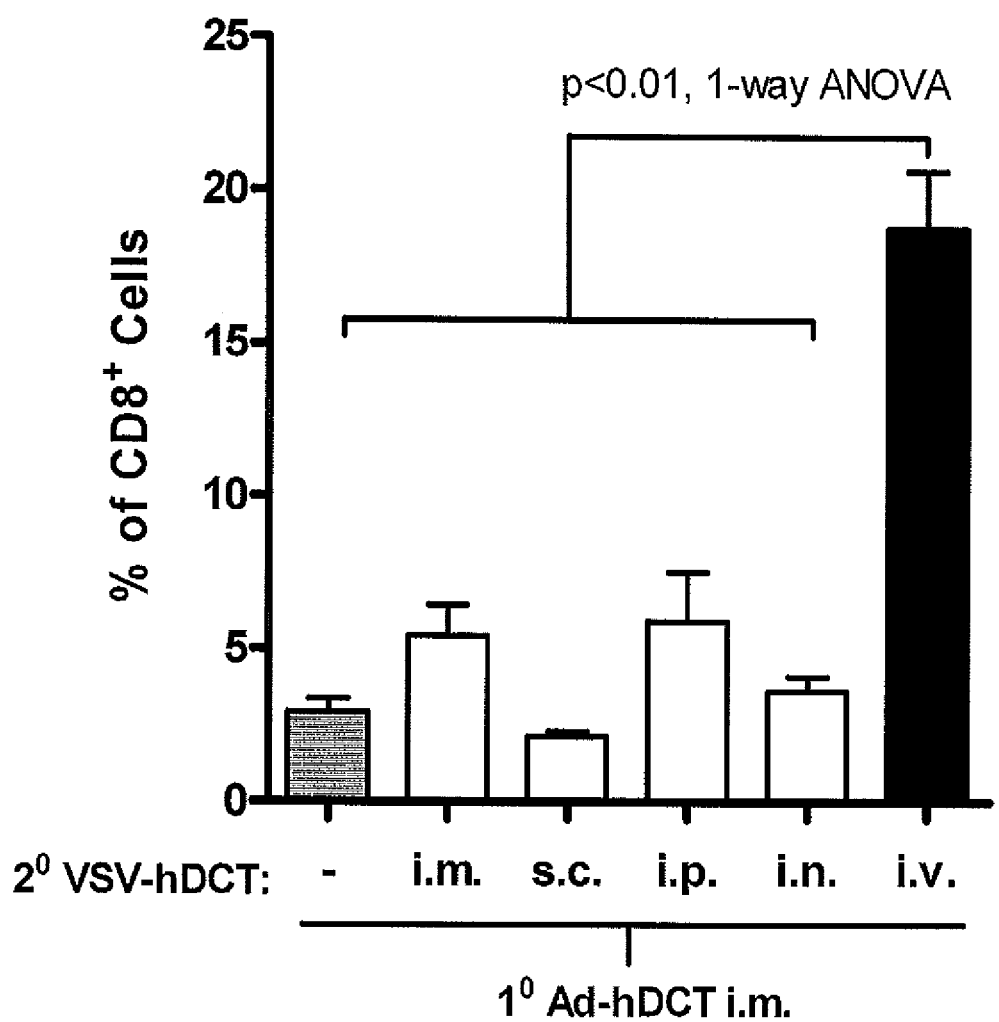
FIG. 11 demonstrates a comparison of delivery routes for the prime boost regimen.

C57BL/6 mice (n=5/group) received i.m. injections of $1 \times 10^8$ pfu of Ad-hDCT on day 0 followed by injections of $1 \times 10^9$ pfu of VSV-hDCT by various routes (i.m. intramuscular, s.c. subcutaneous, i.p. intraperitoneal, i.n. intranasal, i.v. intravenous) on day 14. Seven days later, blood-derived T cell responses to the immunodominant epitope from the melanoma-associated antigen, dopachrome tautomerse (DCT180-188) were measured by flow cytometric analysis of intracellular staining of interferon-gamma following re-stimulation with the peptide 9 (see FIG. 11).

Figure 12:
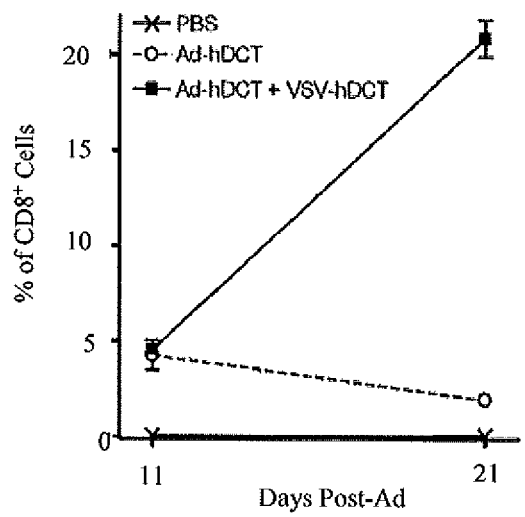
FIG. 12 shows boosting capabilities at different intervals.
Figure 12:
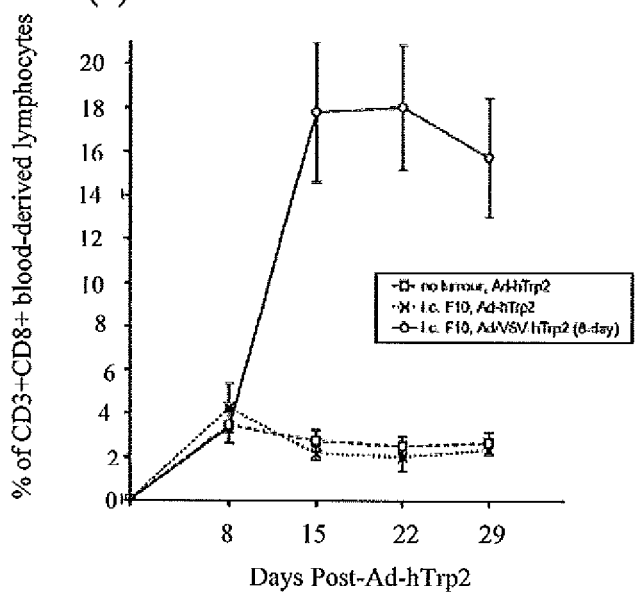

C57BL/6 mice (n=5/group) received i.m. injections of $1 \times 10^8$ pfu of Ad-hDCT on day 0 followed by i.v. injections of $1 \times 10^9$ pfu of VSV-hDCT at the peak of the primary immune response, day 14 (FIG. 12a), or before the peak, day 8 (FIG. 12b) (Note: Ad-induced peak is day 12-14). Seven days later, blood-derived T cell responses to the immunodominant epitope from the melanoma-associated antigen, dopachrome tautomerse (DCT180-188) were measured by flow cytometric analysis of intracellular staining of interferon-gamma following re-stimulation with the peptide. This strategy worked in both tumour-free (FIG. 12a) and tumour-bearing (FIG. 12b; in this case, intracranial B16-F10 melanomas, known to be immunosuppressive) scenarios.

Figure 13:
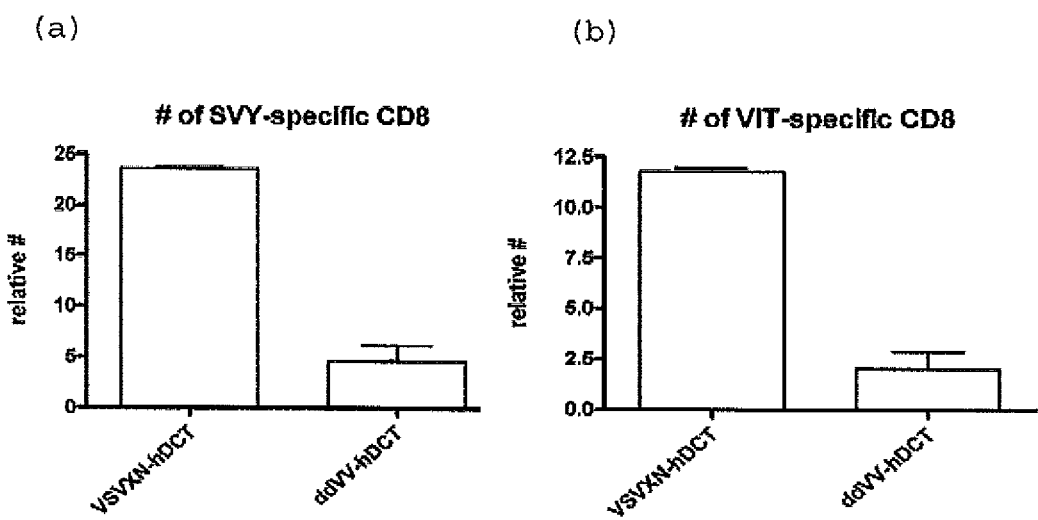
FIG. 13 demonstrates a comparison between the ability of i.v. administered VSV and Vaccinia virus at boosting immune responses.

C57BL/6 mice (n=5/group) received i.m. injections of $1 \times 10^8$ pfu of Ad-hDCT on day 0 followed by i.v. injections of $1 \times 10^7$ pfu of VSV-hDCT or ddVV-hDCT on day 232. Blood-derived T cell responses to the immunodominant (SVY) (FIG. 13a) and second most dominant (VIT) (FIG. 13b) epitopes from the melanoma-associated antigen, dopachrome tautomerse, were measured by flow cytometric analysis of intracellular staining of interferon-gamma following re-stimulation with the peptide.

Figure 14:
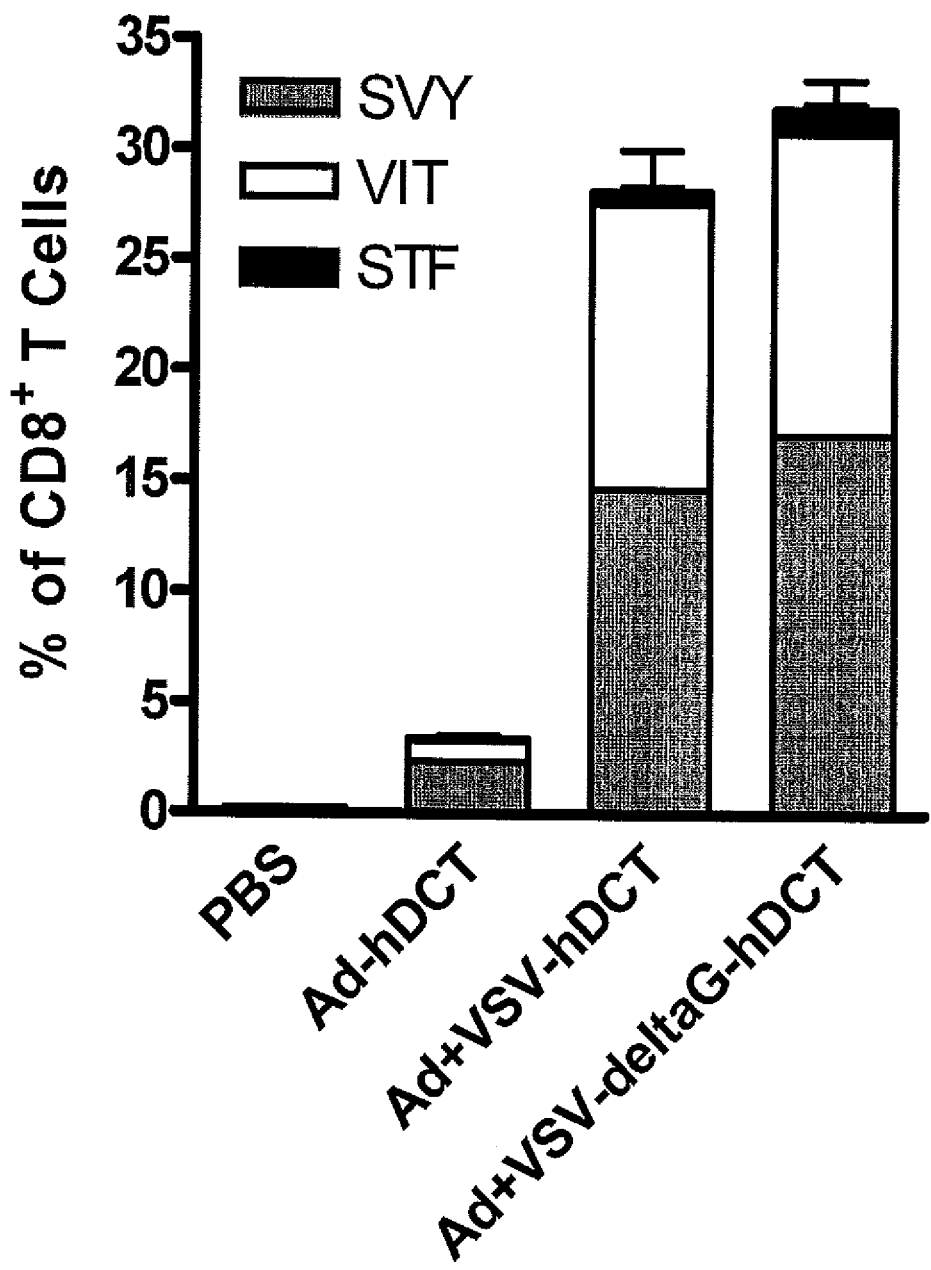
FIG. 14 shows the ability of the G-less (mutant) version of VSV to boost immune responses.

C57BL/6 mice (n=5/group) received i.m. injections of $1 \times 10^8$ pfu of Ad-hDCT on day 0 followed by i.v. injections of $1 \times 10^7$ pfu of VSV-hDCT or VSV-deltaG-hDCT (a version of the vector that leads to a non-productive infection; considered extremely safe) on day 35. Blood-derived T cell responses to the immunodominant (SVY), second most dominant (VIT) and third most dominant (STF) epitopes from the melanoma-associated antigen, dopachrome tautomerse, were measured by flow cytometric analysis of intracellular staining of interferon-gamma following re-stimulation with the peptide (FIG. 14).

Figure 15:
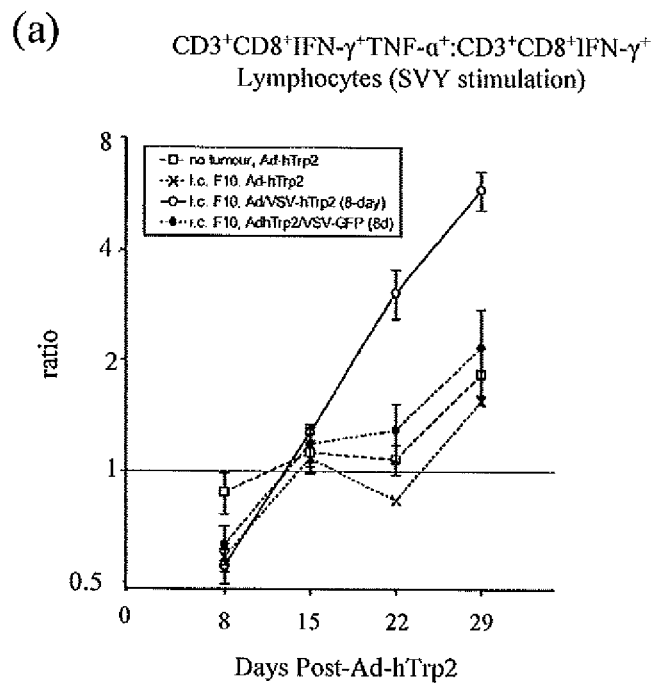
FIG. 15 demonstrates the quality of T cells elicited by the prime boost regimen.
Figure 15:
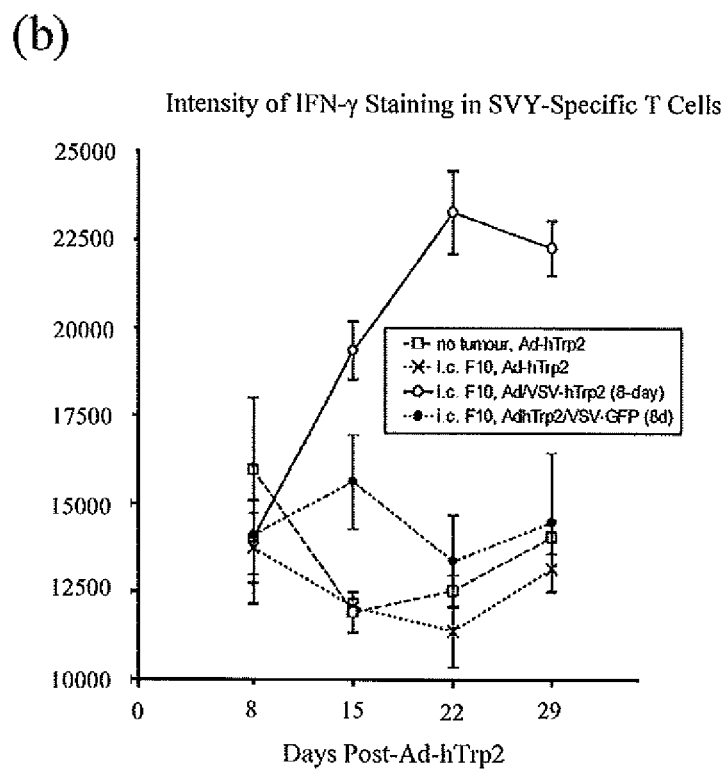

C57BL/6 mice (n=5/group) received i.m. injections of $1 \times 10^8$ pfu of Ad-hDCT on day 0 followed by i.v. injections of $1 \times 10^9$ pfu of VSV-hDCT on day 8. On days 8, 15, 22 and 29 post-Ad, blood-derived T cell responses to the immunodominant (SVY) epitope from the melanoma-associated antigen, dopachrome tautomerse, were measured by flow cytometric analysis of intracellular staining of interferon-gamma following re-stimulation with the peptide. More T cells produced tumour necrosis factor (TNF)-alpha (FIG. 15a) (expressed as a ratio of double cytokine to single cytokine-producing cells) in response to VSV-hDCT boosting as compared to Ad-hDCT alone, with or without the presence of B16-F10 brain melanomas, or Ad+a control VSV vector (VSV-GFP). In addition, each T cell from VSV-hDCT-boosted mice produced more interferon-gamma (FIG. 15b).

Figure 16:
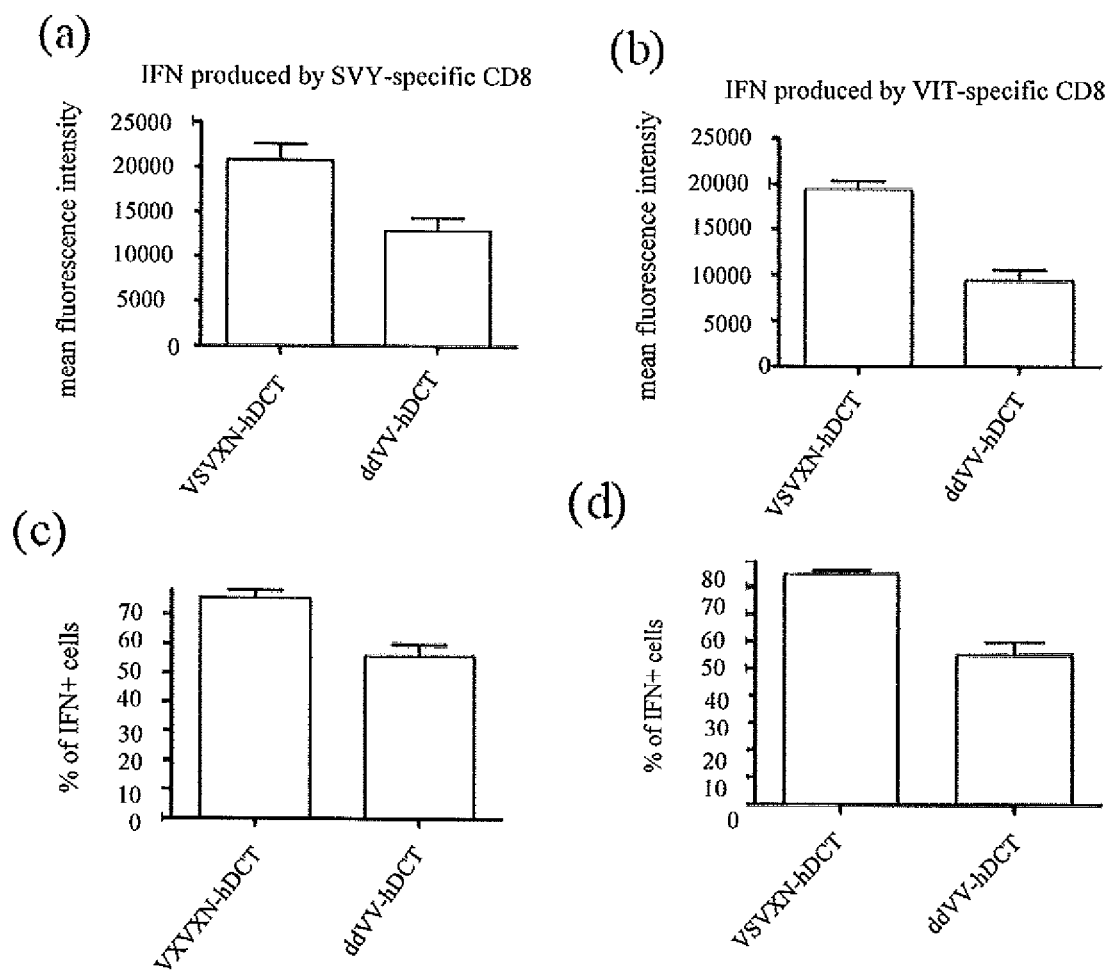
FIG. 16 shows the quality of the T cells elicited by boosting with VSV as compared to boosting with a Vaccinia vector.

C57BL/6 mice (n=5/group) received i.m. injections of $1 \times 10^8$ pfu of Ad-hDCT on day 0 followed by i.v. injections of $1 \times 10^7$ pfu of VSV-hDCT or ddVV-hDCT on day 232. Blood-derived T cell responses to the immunodominant (SVY) (FIGS. 16a, c) and second most dominant (VIT) (FIGS. 16b, d) epitopes from the melanoma-associated antigen, dopachrome tautomerse, were measured by flow cytometric analysis of intracellular staining of interferon-gamma following re-stimulation with the peptide. The amount of interferon (IFN) gamma produced on a per-cell basis (FIGS. 16a, b) and the proportion of IFN-gamma-producing cells that also secreted tumour necrosis factor (TNF) alpha (FIGS. 16c, d) were evaluated.

Figure 17:
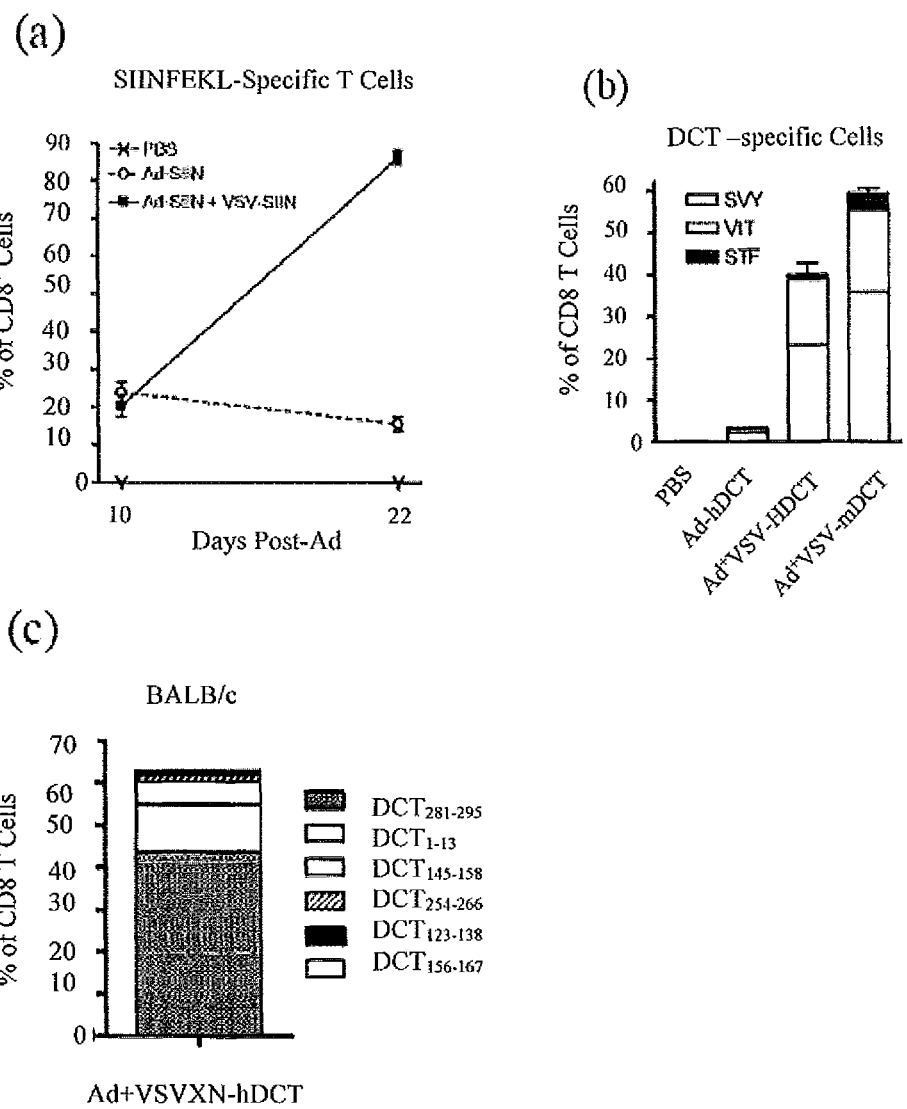
FIG. 17 demonstrates the T cell response of the boosting regimen using different antigens and host strains.

C57BL/6 (FIGS. 17a, b) or BALB/c (FIG. 17c) mice (n=5/group) received i.m. injections of $1 \times 10^8$ pfu of Ad-hDCT on day 0 followed by i.v. injections of $1 \times 10^9$ pfu of VSV-SIIN (FIG. 14a) or VSV-hDCT (FIGS. 17b, c) or VSV-murine DCT (VSV-mDCT) (FIG. 17b) 17 days (FIG. 17a) or 35 days later (FIGS. 17b, e). Five days post-VSV, blood-derived T cell responses to SIINFEKL (FIG. 17a) or the melanoma-associated antigen, dopachrome tautomerse (FIGS. 17b, c) were measured by flow cytometric analysis of intracellular staining of interferon-gamma following re-stimulation with the peptide.

Figure 18:
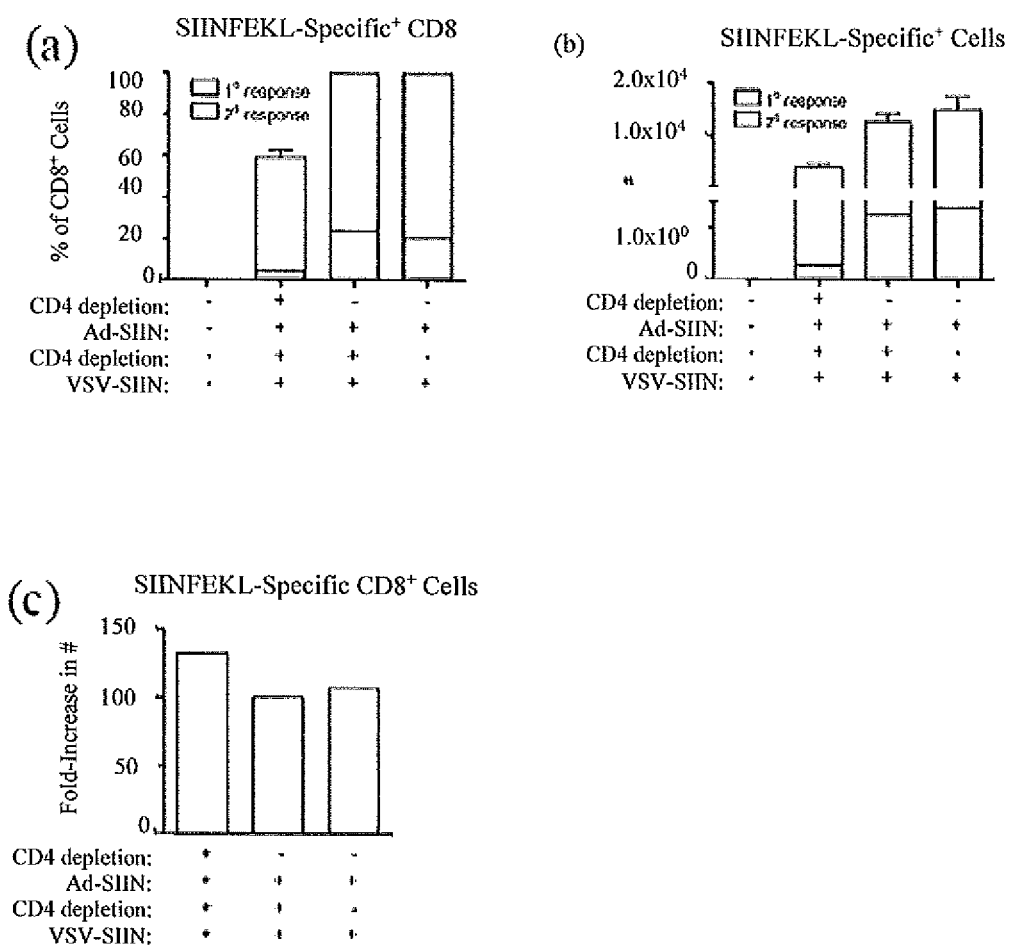
FIG. 18 shows that the boosting effect mediated by i.v. VSV is CD4+ T cells independent.

C57BL/6 mice (n=5/group) received i.m. injections of $1 \times 10^8$ pfu of Ad-SIIN on day 0 followed by i.v. injections of $1 \times 10^9$ pfu of VSV-SIIN on day 17. Ten days post-Ad (1° response) and five days post-VSV (2° response), blood-derived T cell responses to SIINFEKL where measured by tetramer staining. Results show the frequency (FIG. 18a), number (FIG. 18b) and fold-increase in these responses.

Figure 19:
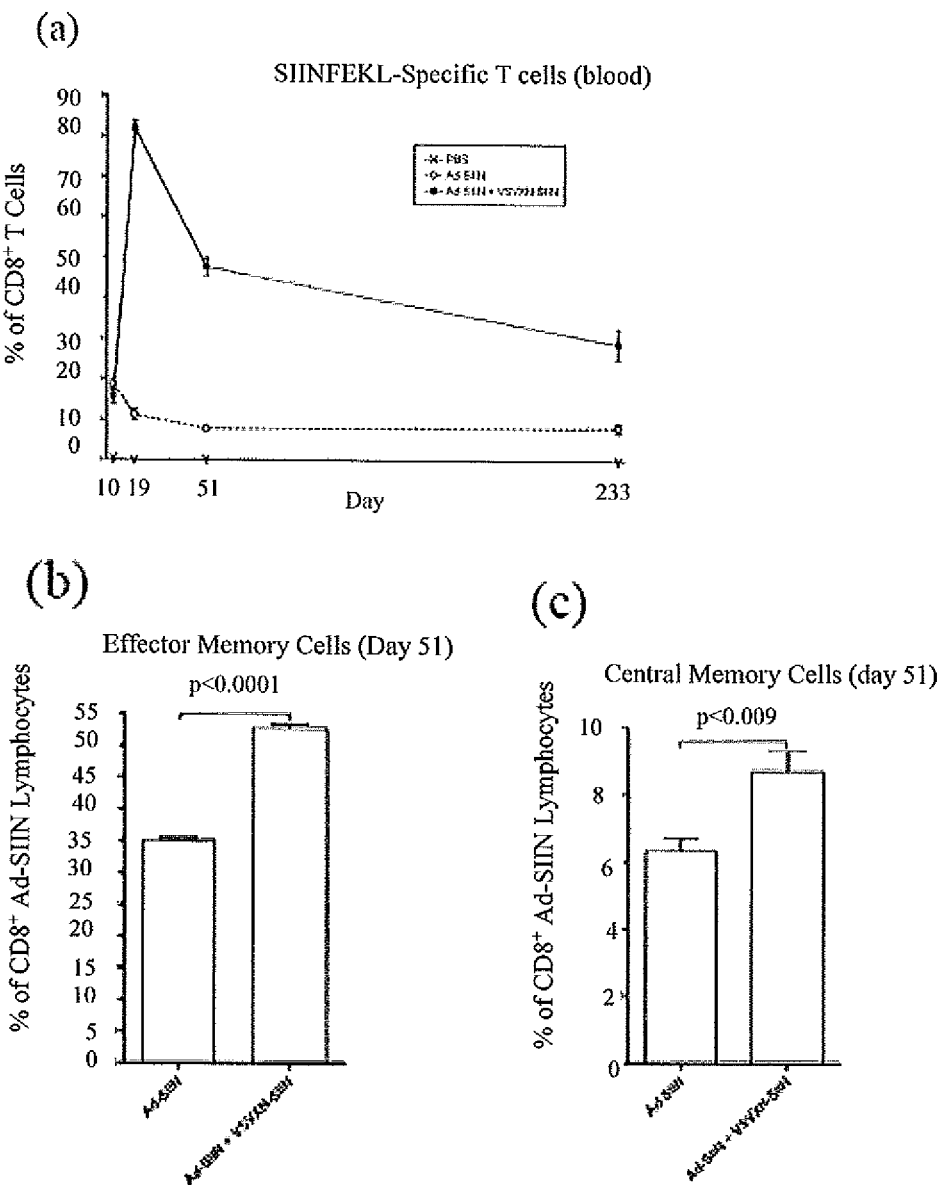
FIG. 19 demonstrates the durability of the secondary immune response and proportion of effector cells that have been converted to memory cells.

C57BL/6 mice (n=5/group) received i.m. injections of $1 \times 10^8$ pfu of Ad-SIIN on day 0 followed by i.v. injections of $1 \times 10^9$ pfu of VSV-SIIN on day 14. On days 10, 19, 51 and 233, blood-derived T cell responses to SIINFEKL where measured by tetramer staining. Longevity of the response is shown in (FIG. 19a). The proportion of effector memory (defined as CD127+CD62L−) (FIG. 19b) and central memory (CD127+CD62L+) (FIG. 19c) SIINFEKL-specific cells were assessed on day 51.

Figure 20:
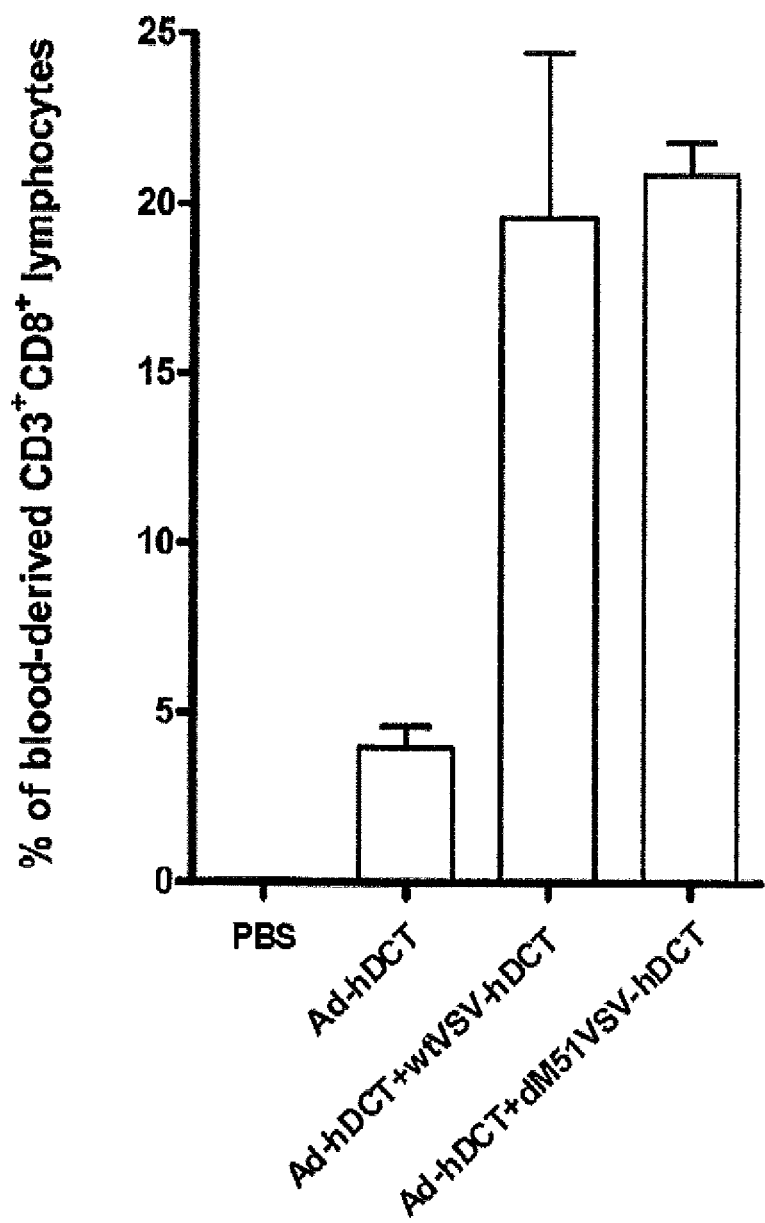
FIG. 20 shows that an attenuated, interferon-inducing mutant VSV vaccine boosts equivalently to wildtype VSV.

C57BL/6 mice (n=5/group) received i.m. injections of $1 \times 10^8$ pfu of Ad-SIIN on day 0 followed by i.v. injections of $1 \times 10^9$ pfu of either wtVSV-hDCT or deltaM51VSV-hDCT on day 14. Five days post-VSV, blood-derived T responses were measured by flow cytometric analysis of intracellular staining of interferon-gamma following re-stimulation with the peptide (FIG. 20).

Figure 21:
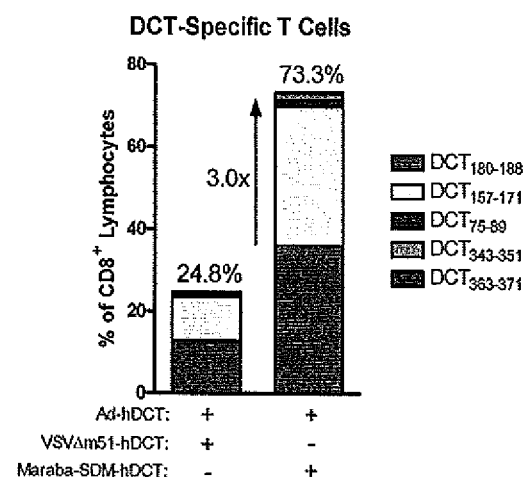
FIG. 21 compares the immune response when VSV and Maraba-based vectors are utilized to deliver a DCT antigen boost.
Figure 21:
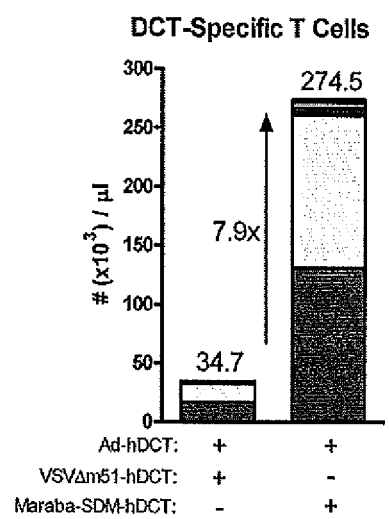
Figure 22:
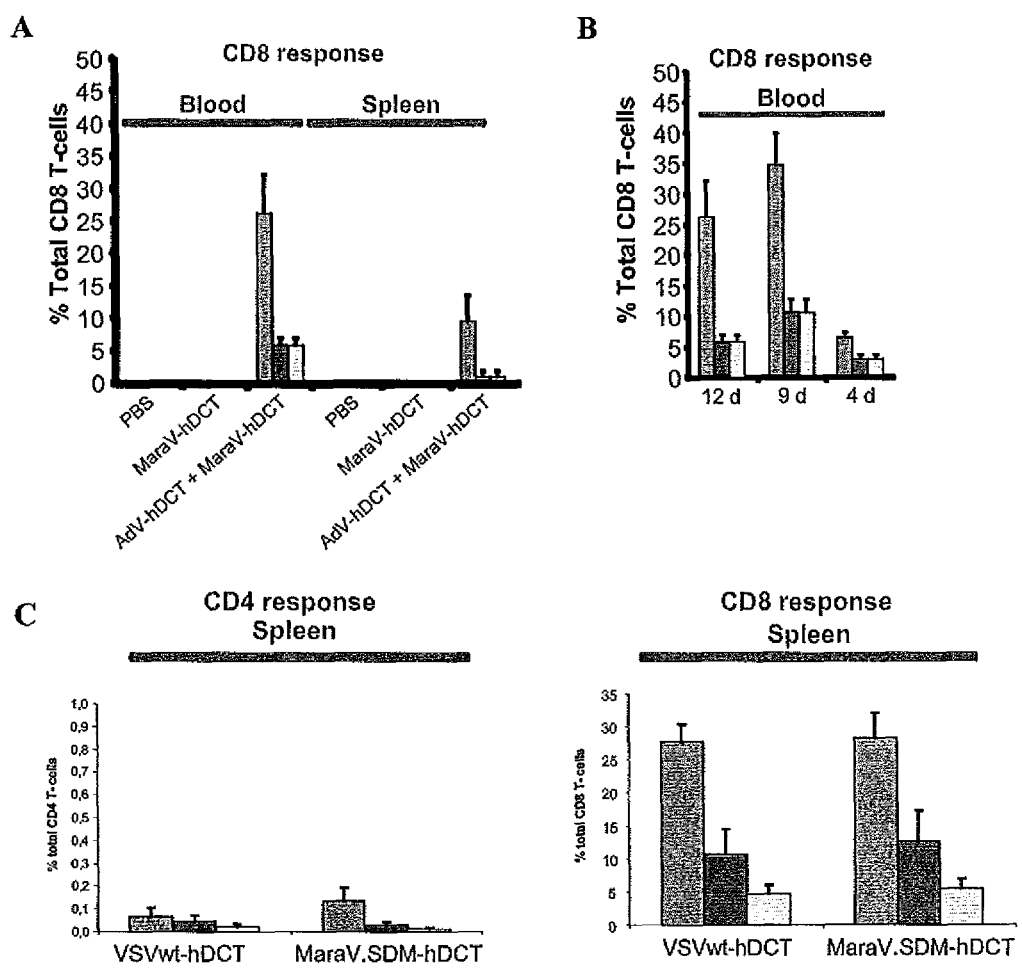
FIG. 22 illustrates the immune responses in blood (A & B) and spleen (C) when Ad and Maraba vectors are used to deliver an antigen and Maraba and VSV vectors are used to boost antigen immunity.

C57/B6 mice were primed with Ad-hDCT and then boosted with an intravenous dose of either VSV-hDCT or Maraba-hDCT 14 days later. Immune analysis of CD8+ T cell responses were measured in peripheral blood. At an equivalent dose the response induced by Maraba vaccination was 3-8 fold as large as the VSV-induced responses versus transgene (FIG. 21). In a further experiment, C57/B6 mice were either primed with Maraba-hDCT ($2 \times 10^9$ PFU IV) or primed with Ad-hDCT ($1 \times 10^8$ PFU IM) and boosted with Maraba-hDCT ($2 \times 10^9$ PFU IV). Immune responses were measured in blood and spleen 5 days later (three bars per treatment, left bar is IFNγ+, middle is TNFα+ and right bar is double positive in each case) as shown in FIG. 22A. Maraba-hDCT administered IV 9 or 12 days post-Ad priming (at the peak of the Ad-induced effector phase) can still boost immune responses (FIG. 22B). Intravenously administered Maraba-hDCT and VSV-hDCT both significantly boost immune responses in BalB-C mice (mice treated as in A, bars represent IFNγ+, TNFα+ and double+left to right for each treatment) as shown in FIG. 22C.

Figure 23:
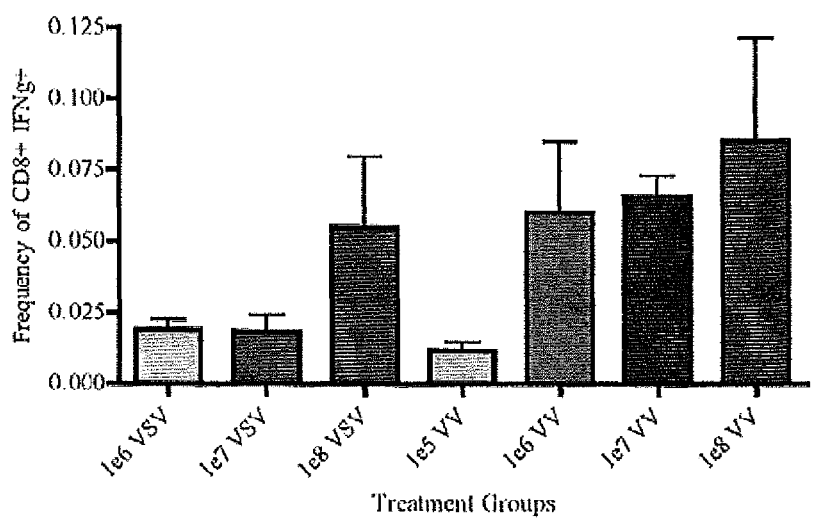
FIG. 23 illustrates the immune response with various doses of antigen (A) to establish a pre-existing immunity and the effect of a VSV boost on each (B)
Figure 23:
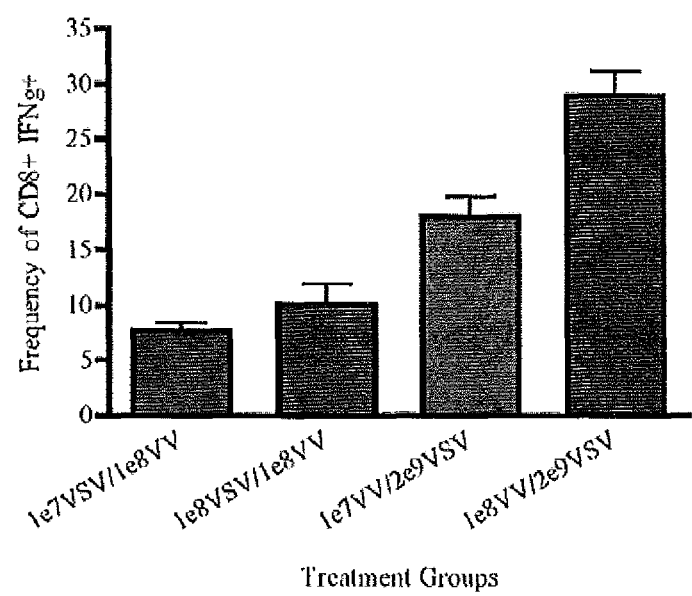

C57/B6 mice were primed with varying doses of VSV and vaccinia expressing SIINFEKL-luciferase to prime a response versus this OVA epitope (FIG. 23A) and subsequently boosted with intravenously administered VSV-hDCT. SIINFEKL-specific T cell responses were measured and shown in FIG. 23 to be significantly enhanced by the subsequent VSV boost.

Figure 24:
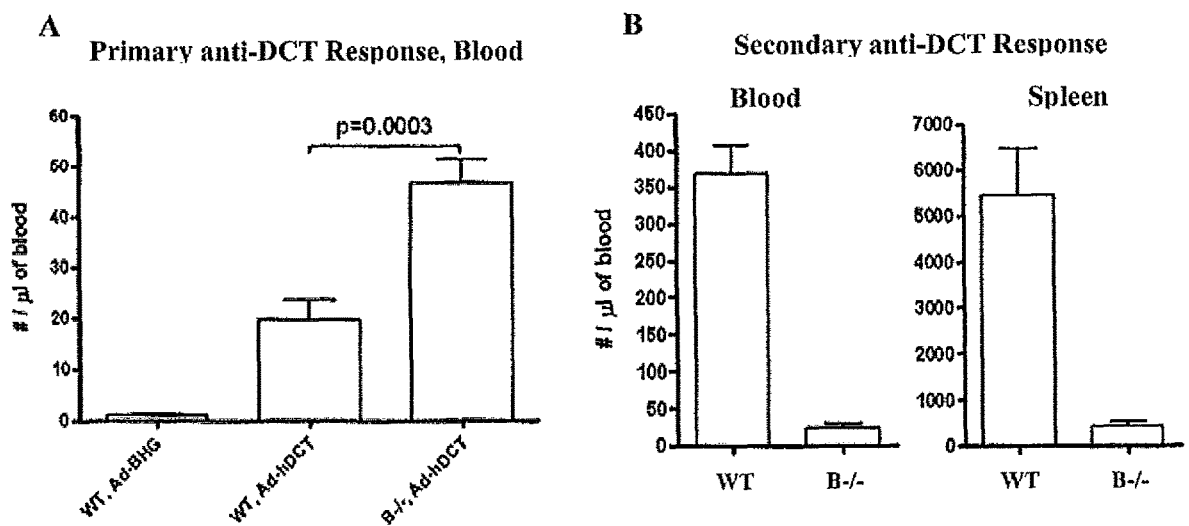
FIG. 24 compares the primary immune response to an antigen in wild-type vs B cell deficient mice (A) and the immune response in blood and spleen following an antigen boost (B)
Figure 25:
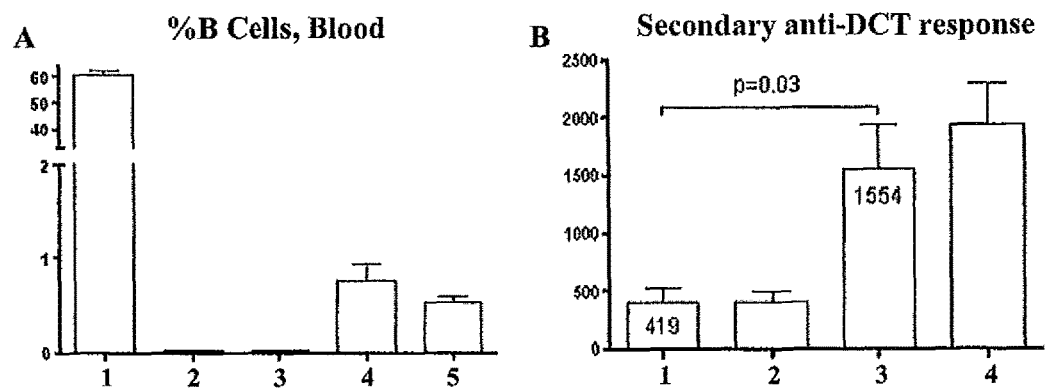
FIG. 25 illustrates the effect of B cell reconstitution (A) on an antigen boost (B).

C57/B6 mice were given a single intravenous dose of $2 \times 10^9$ PFU VSV-GFP and 24 hours later the spleens were collected for flow cytometric analysis. 61.3% of bulk splenocytes were B220+CD19+ indicative of B cells. 50.8% of the GFP positive cells are B220+CD19+ and are detected in the B cell fraction, Wildtype C57-B6 and B cell –/– mice were vaccinated with Ad-hDCT to prime an anti-DCT immune response as measured by DCT-specific CD8+ T cells in the blood (FIG. 24A). The secondary response was measured following intravenous administration of VSV-hDCT. Numbers of IFN γ+ CD8+ T cells as measured by intracellular staining are indicated +/– SEM. (FIG. 24B) indicated dependence of boost on B cells, B cells from wildtype mice and/or immune serum was adoptively transferred to B cell-deficient mice. B cells were measured as a percentage of peripheral blood lymphocyte in. 1) wt control 2) B–/– plus VSV 3) B–/– plus VSV plus serum 4) B–/– plus B cells VSV and 5) B–/– plus B cells plus serum plus VSV as shown in FIG. 25A. Anti-DCT T cell responses were measured in reconstituted B cell-deficient mice following VSV boosting. Numbers of IFNγ+ CD8+ T cells are indicated +/–SEM. Lanes: 1) B–/– plus VSV 2) B–/– plus VSV plus serum 3) B–/– plus B cells VSV and 4) B–/– plus B cells plus serum plus VSV (FIG. 25B) showing enhanced responses in B cells, VSV-SIIN ($2 \times 10^9$ pfu) was injected intravenously into a C57/B6 mouse, and 24 hours later, spleens were harvested and CD19 positive cells were purified from total splenocytes. CD19+ cells were co-cultured with a DKL cell line. Activation of T cells cocultured with CD19+ cells from VSV-SIIN immunized mouse, CD19– cells from VSV-SIIN immunized mouse, CD19+ cells from VSV-SIIN immunized mouse co-cultured with DKL in the presence of SIIN peptide (positive control) and negative control. The results show that virus infected B cells can stimulate T cell to produce IFN-γ.

Splenic B cells were isolated from C57/B6 mice and cultured in muIL2 for 4 days and then loaded with either VSV-SIINFEKL/luciferase or Ad-SIINFEKL/luciferase (2 hour infection, washed and collected). These loaded B cells were administered IV to naive or primed recipients. T cell responses were measured 5 days later. T-cells from mice primed with vaccinia-SIINFEKL/luciferase showed response to SIINFEKL peptide. T-cells from mice primed with VSV-SIINFEKL/luciferase loaded B cells showed response to SIINFEKL peptide. T-cells from mice primed with vAd-SIINFEKL/luciferase loaded B cells showed a minimal response to SIINFEKL peptide. T-cells from mice primed with vaccinia-SIINFEKL/luciferase and then boosted with VSV-SIINFEKL/luciferase loaded B cells showed response to SIINFEKL peptide. T-cells from mice primed with vaccinia-SIINFEKL/luciferase and then boosted with Ad-SIINFEKL/luciferase loaded B cells showed response to SIINFEKL peptide (TNFα Yaxis, IFNγ Xaxis in each case).

Discussion

Mice were immunized with Adenovirus via intramuscular injection for 14 days. A single dose of recombinant VSV was delivered to mice as the boost portion of a prime boost vaccination regimen by either intramuscular, subcutaneous, intraperitoneal, intranasal or intravenous routes. Antigen specific T cell responses were measured 7 days later and it was noted that there was a significantly larger T cell response when VSV was delivered intravenously (see FIG. 11).

The timing of the immune response boost elicited by VSV was tested in this prime boost vaccination model. The boost was delivered intravenously at the peak of the primary immune response (day 14) or at day 8, preceding the peak (during the effector phase). T cell responses measured 7 days later revealed that the VSV boost was capable of boosting the immune response at and before the peak of the primary immune response. This was demonstrated in both tumour free and tumour bearing mice, and therefore immunosuppressive environments (see FIG. 12). It is notable that the booster was effective during the effector phase. Generally, the effector T cells wane before such a booster vector works.

The immune boosting capability of VSV was compared to a control Vaccinia virus. The boost was performed at 232 days following the initial prime (this prolonged interval allows 100-fold lower doses of VSV to achieve the same level of T cell boosting as demonstrated above) and the T cell response to 2 different antigen specific peptides was tested. The boosting ability of the VSV, as measured by blood-derived T cell responses was found to be substantially better than that of the Vaccinia virus for both antigen peptides tested (see FIG. 13).

A mutant version of VSV which can replicate its genome and express genes within cells that are initially infected but is unable to produce infectious progeny was tested for its ability to boost the immune response. Blood derived T cell responses to 3 dominant epitopes of the antigen used in the prime boost protocol indicated that the mutant VSV boosted the immune response as effectively as the wlldtype version (see FIG. 14). This indicates that a safer version of the virus which cannot spread can be used for boosting an immune response.

The quality of T cells elicited by boosting with VSV, as measured by production of multiple cytokines as well as amount of cytokine production per cell was evaluated for the VSV boost. The quality was compared to T cells elicited by a prime vaccination alone or a boost with a VSV control vector (no inserted Ag transgene). T cells generated by the antigen-specific VSV boost produced multiple cytokines and a greater amount of interferon-gamma (see FIG. 15). The quality of T cells elicited by the antigen-containing VSV boost was further compared to a Vaccinia virus boost. Again, the T cells from the VSV boost population produced a greater amount of interferon gamma and also secreted higher amounts of tumour necrosis factor alpha (see FIG. 16).

Two different mouse strains were tested with the prime boost VSV regimen, as were two different antigens. In all scenarios, the massive immune boost following VSV administration was observed (see FIG. 17).

The requirement for CD4+ helper T cells in the VSV mediated immune boost was tested. T cell responses following the boost were examined both with and without CD4 cell depletion. Depletion had an impact on the primary immune response, but not on the secondary response as measured by the percent, number and fold-increase in CD8+ T cells (see FIG. 18). The VSV prime boost method therefore holds promise for treating immunocompromised patients such as those afflicted with AIDS/HIV infection.

The durability of the boosted immune response was tested at 10, 19, 51 and 233 days following the boost. The T cell response measured at these time points indicates that the immune response was maintained long term. An evaluation of the proportion of effector memory and central memory cells at day 51 indicates there was a conversion of a higher proportion of effector cells into memory phenotype as compared to a primed response alone (see FIG. 19). Effector cells are no longer needed once antigen is cleared. A larger pool of memory cells at this point, especially central memory cells, will ensure a better re-expansion when encountering the antigen again.

A VSV vector bearing a deltaM51 mutation in the matrix protein rendering it unable to block interferon production, and thus referred to as an interferon-inducing mutant can be used to generate a similar boosting effect. Mice were primed with Ad-hDCT with a subsequent boost of either wildtype VSV-hDCT (wtVSV-hDCT) or deltaM51 VSV-hDCT (dM51 VSV-hDCT) and DCT-specific T cells were measured in the blood (see FIG. 20). The deltaM51 VSV vector is attenuated by interferon induction in vivo and is thus both a safer vector and has associated oncolytic properties. This demonstrates that various means can be utilized to attenuate VSV while retaining the ability to boost immune responses following intravenous delivery.

VSV-vectored vaccines are particularly potent boosting agents when administered intravenously. The unique and notable features of this approach include the magnitude of response, durability of memory, preferred route of delivery, CD4 T cell independence, ability to boost the immune response early (during the effector phase), ability to elicit a superior quality of T cells, boosting of responses to subdominant epitopes and the adaptability to safer, attenuated vectors. This strategy may be applied to any desired antigen including, for example, foreign antigens derived from pathogens as well as autoantigens, oncofetal antigens and neoantigens targeting tumors. The boost may be used in conjunction with any priming strategy to boost T cell and antibody responses for both prophylactic and therapeutic vaccination. As well, other members of the vesiculovirus or rhabdoviral families can be used in place of VSV as the boosting vector. Various non-replicating or mutant versions of these boosting viruses may also be used as boosting vectors.

IV administered VSV infects B cells in the spleen. The boosting ability of intravenously administered VSV vectors is B cell dependent. IV administered VSV infects B cells in the spleen. When these cells are isolated following VSV administration, they are shown to present transgene antigen to specific T cells ex vivo. B cells loaded with a VSV vaccine ex vivo is a superior vaccination platform to vaccinate both naïve and primed animals. Other viruses with a B cell tropism may also be used to achieve these effects.

Relevant portions of references referred to herein are incorporated by reference.

We claim:

1. A method of treating a mammal having a tumour that expresses a tumour antigen, said method comprising
   1) first, vaccinating said mammal with the tumour antigen or a nucleotide sequence capable of expressing the tumour antigen in the absence of an oncolytic rhabdoviral vector, said vaccinating being capable of generating an immunity to the tumour antigen; and
   2) second, administering to the mammal an oncolytic rhabdoviral vector, wherein said oncolytic rhabdoviral vector comprises a nucleic acid capable of expressing the tumour antigen, and wherein the oncolytic rhabdoviral vector is not vesicular stomatitis virus (VSV).

2. The method as defined in claim 1, wherein the tumour antigen is a tumour-associated antigen.

3. The method as defined in claim 1, wherein the tumour antigen or the nucleotide sequence capable of expressing the tumour antigen is selected from the group consisting of an oncofetal antigen, a surface glycoprotein, a cell surface marker, a melanoma-associated antigen (MAGE), cancer-testes antigen, an oncogene, a viral oncogene, dopachrome tautomerase (DCT), GP100, MART1, alphafetoprotein (AFP) and carcinoembryonic antigen (CEA).

4. The method of claim 3, wherein said tumour antigen is encoded by a viral oncogene.

5. The method of claim 4, wherein the viral oncogene comprises HPV E6.

6. The method of claim 4, wherein the viral oncogene comprises HPV E7.

7. The method of claim 4, wherein said viral oncogene comprises HPV E6 and HPV E7.

8. The method of claim 3, wherein said tumour antigen is a melanoma-associated antigen.

9. The method as defined in claim 1, wherein the oncolytic rhabdoviral vector is selected from the group consisting of: a Vesiculovirus, an Ephemerovirus, a Cytorhabdovirus, a Nucleorhabdovirus and a Lyssavirus.

10. The method as defined in claim 9, wherein the Vesiculovirus is a Maraba virus.

11. The method as defined in claim 1, wherein the tumour antigen or the nucleotide sequence capable of expressing the tumour antigen is first administered at least about 4 days prior to the administration of the oncolytic rhabdoviral vector.

12. The method of claim 1, wherein the oncolytic rhabdoviral vector is administered intravenously, intramuscularly or intranasally.

13. The method of claim 12, wherein the oncolytic rhabdoviral vector is administered intravenously.

14. The method of claim 1, wherein the cancer is a melanoma, sarcoma, lymphoma, leukemia, or carcinoma.

15. The method of claim 14, wherein said cancer is a carcinoma.

16. The method of claim 15, wherein the carcinoma is brain cancer, breast cancer, liver cancer, stomach cancer, or colon cancer.

17. The method of claim 16, wherein said cancer is breast cancer.

18. The method of claim 1, wherein the tumour antigen comprises HPV E6.

19. The method of claim 1, wherein the tumour antigen comprises HPV E7.

20. The method of claim 1, wherein said tumour antigen comprises HPV E6 and HPV E7.

21. The method of claim 1, wherein 1) comprises vaccinating said mammal with the tumour antigen in the presence of a suitable adjuvant.

22. The method of claim 1, wherein 1) comprises vaccinating said mammal with an adenoviral vector comprising a nucleotide sequence capable of expressing the tumour antigen.

23. A kit for use in a method of claim 1, comprising a tumour antigen, or a vector expressing a tumour antigen, in an amount suitable to induce an immune response in a mammal, and an oncolytic rhabdoviral vector comprising a nucleic acid capable of expressing the tumour antigen in an amount suitable to enhance the immune response, wherein the oncolytic rhabdoviral vector is not vesicular stomatitis virus (VSV).

* * * * *